(12) United States Patent
Zhang et al.

(10) Patent No.: US 12,037,584 B2
(45) Date of Patent: Jul. 16, 2024

(54) POLYNUCLEOTIDE AND METHOD FOR CONTROLLING INSECT INFESTATION

(71) Applicant: BEIJING DABEINONG BIOTECHNOLOGY CO., LTD., Beijing (CN)

(72) Inventors: Aihong Zhang, Beijing (CN); Derong Ding, Beijing (CN); Qing Tao, Beijing (CN); Xiaojiao Li, Beijing (CN)

(73) Assignee: BEIJING DABEINONG BIOTECHNOLOGY CO., LTD. (CN)

( * ) Notice: Subject to any disclaimer, the term of this patent is extended or adjusted under 35 U.S.C. 154(b) by 0 days.

(21) Appl. No.: 16/972,896

(22) PCT Filed: May 29, 2019

(86) PCT No.: PCT/CN2019/088925
§ 371 (c)(1),
(2) Date: Dec. 7, 2020

(87) PCT Pub. No.: WO2019/237919
PCT Pub. Date: Dec. 19, 2019

(65) Prior Publication Data
US 2021/0246445 A1 Aug. 12, 2021

(30) Foreign Application Priority Data
Jun. 15, 2018 (CN) .......................... 201810618043.4

(51) Int. Cl.
*C12N 15/82* (2006.01)
*A01N 63/60* (2020.01)
*C12N 15/113* (2010.01)

(52) U.S. Cl.
CPC ............ *C12N 15/113* (2013.01); *A01N 63/60* (2020.01); *C12N 15/8218* (2013.01); *C12N 15/8286* (2013.01); *C12N 2310/14* (2013.01)

(58) Field of Classification Search
CPC .................................................. C12N 15/113
USPC ....................................................... 800/279
See application file for complete search history.

(56) References Cited

U.S. PATENT DOCUMENTS

2016/0244779 A1\* 8/2016 Bell .................. C12N 15/8261
2018/0200281 A1\* 7/2018 Donohue ................ A01C 1/06

FOREIGN PATENT DOCUMENTS

CN           101045728 A  \* 10/2007
WO         2018026773 A1     2/2018
WO    WO-2018026773 A1 \*   2/2018  ........... A61K 31/713

OTHER PUBLICATIONS

Mogilicherla et al (Scientific Reports, 2018, 8:3720; published online Feb. 27, 2018) (Year: 2018).\*
Batiz et al (PLoS ONE, 2009, 4(3): e4963) (Year: 2009).\*
BLAST sequence search results (accessed online Apr. 9, 2022). (Year: 2022).\*
Hague, B. et al. "Single Tube, High Throughput Cloning of Inverted Repeat Constructs for Double-Stranded RNA Expression." Plos one., vol. 4, No. 9, Sep. 28, 2009 (Sep. 28, 2009).
International Search Report (English & Chinese) of the International Searching Authority issued in PCT/CN2019/088925, dated Sep. 4, 2019; ISA/CN.
Canadian Office Action issued in corresponding Application No. 3,103,009 dated Jan. 31, 2023 (5 Pages).

\* cited by examiner

*Primary Examiner* — Li Zheng
(74) *Attorney, Agent, or Firm* — Harness, Dickey & Pierce, P.L.C.

(57) ABSTRACT

An isolated polynucleotide includes: (a) a polynucleotide sequence as shown in SEQ ID NO: 1; or (b) a polynucleotide sequence comprising at least 15 or 17 or 19 or 21 contiguous nucleotides of SEQ ID NO: 1, wherein the ingestion, by *Coleoptera* insect pests, of a double-stranded RNA comprising at least one strand complementary to the polynucleotide sequence inhibits the growth of the *Coleoptera* insect pests; or (c) any one of the polynucleotide sequence as shown in SEQ ID NO: 3 to SEQ ID NO: 6; or (d) a polynucleotide sequence hybridized with the polynucleotide sequence defined in (a), (b) or (c) mentioned above under stringent conditions. Multiple target sequences of the target gene c46312 control the *Coleoptera* insect pest *Monolepta hieroglyphica*.

18 Claims, 1 Drawing Sheet
Specification includes a Sequence Listing.

POLYNUCLEOTIDE AND METHOD FOR CONTROLLING INSECT INFESTATION

CROSS REFERENCE TO RELATED APPLICATIONS

This application is a U.S. National Phase application of International Application No. PCT/CN2019/088925, filed on May 29, 2019, which claims priority to Chinese Patent Application No. 201810618043.4, filed on Jun. 15, 2018. The entire disclosures of the above applications are expressly incorporated by reference herein.

FIELD OF THE INVENTION

The present invention relates to the field of plant protection, especially crop protection. In particular, the present invention relates to a polynucleotide and method for controlling insect invasions, especially to a method for controlling *Monolepta hieroglyphica* (Motschulsky) invasions by reducing or silencing the expression of a target sequence in the *Monolepta hieroglyphica* (Motschulsky) body using the RNAi technology.

BACKGROUND

Crops are usually the targets of insect attacks. In the last few decades, there has been some substantive progress in developing more effective methods and compositions for controlling insect invasions in crops. For example, chemical pesticides, microbial pesticides, and genetic engineering methods have been used to control pest invasions.

Chemical pesticides are relatively effective means for controlling pest invasions. Nevertheless, the use of chemical pesticides also has many disadvantages. Firstly, chemical pesticides are non-selective, and as people intend to apply chemical pesticides for controlling insects that are harmful to a variety of crops and other plants, the chemical pesticides also cause damage to non-target organisms, such as earthworms, due to their deficiency in selectivity. Moreover, after applying chemical pesticides for a period of time, the field usually becomes barren. Chemical pesticides will be present in the environment persistently, and will usually be metabolized slowly. Such a slow metabolism results in the presence of chemical pesticide residues in the crops and environment, which will be accumulated in the food chain, particularly in the food chain of higher carnivorous animals. The accumulation of these chemical pesticides results in the induction of diseases in higher species, for example cancers in humans. Therefore, there is a strong demand for an environmentally-friendly method for controlling or eradicating insect invasions in crop production, i.e., a selective, environmentally-friendly method with biodegradability, which can also be used well in a pest resistance management system.

In the last few decades, development of an effective method for controlling plant insect pests has achieved substantive progress. Chemical pesticides are very effective for eradicating plant pests; however, these pesticides also act on non-target insects, and furthermore, chemical pesticides are present in the environment persistently, which not only causes irreversible environmental pollution, but also results in the emergence of drug-resistant insects. Microbial pesticides, particularly pesticides obtained from the strain of *Bacillus thuringiensis* (abbreviated as Bt), play an important role in agricultural production as a substitute for chemical pesticides, and have a certain insecticidal activity on insects including *Lepidoptera, Diptera, Coleoptera*, etc. Nevertheless, microbial pesticides have a relatively high requirement for the pesticide application environment, and if the environment is not suitable for the growth of these microorganisms, repeated application needs to be performed during production, and in some cases, repeated application cannot even achieve the purpose of controlling pests, thereby greatly increasing the production cost. Some transgenic plants which have enhanced resistance to the pests can be obtained by introducing one or more genes encoding Bt insecticidal proteins into the plants through genetic engineering, for example, genetically engineered maize and cotton plants capable of producing Cry toxins have been widely used in agricultural production in the USA and provide the farmers with an alternative solution of traditional pest-controlling methods. Nevertheless, the currently developed transgenic crops containing Cry toxins can only be used for preventing and controlling a narrow range of *Coleoptera* pests, such as corn rootworm and Colorado potato beetle. Nevertheless, there has been no relevant report on the application of Cry toxins for the control of *Monolepta hieroglyphica* (Motschulsky), one of the major pests of corn. In the meantime, *Monolepta hieroglyphica* (Motschulsky) is present as eggs in the soil through the winter, and in June of the following year the larvae hatched from the eggs also move actively in the soil. With the large-scale popularity of straw return-to-field measures in recent years, it has been increasingly difficult year by year to control *Monolepta hieroglyphica* (Motschulsky) by using chemical pesticides. In particular, in late July and early August when adult insects of *Monolepta hieroglyphica* (Motschulsky) emerge from the ground and the corn has grown to certain height, it is more difficult to control the adult insects by applying chemical pesticides.

RNA interference or RNAi is a method for down-regulating gene expression in a sequence-specific manner in a cell or a whole organism environment, in which the purpose of directed interference with the expression of a target gene can be achieved by the specific targeting selection and efficient mRNA repression. Although it is known in the art that the RNAi technology can be used for preventing and controlling pests, as there are numerous kinds of insects, this technology not only differs in its significantly different effects on distinct insects, and a key factor for using such a technique as a measure for controlling insect invasions further lies in selecting the mostly suitable target gene, i.e., a gene, the function of which is lost, thereby resulting in severe disruption of the essential biological processes and/or death of organisms. Therefore, the present invention achieves the control of insect invasions, particularly the control of insect invasions in a plant, by means of down-regulating a specific target gene in a pest.

SUMMARY

The object of the present invention is to provide a polynucleotide and method for controlling insect invasions, i.e., down-regulating the expression of a target gene using the RNAi technology in a manner of weakening the abilities of an insect to survive, grow, reproduce, colonize in a specific environment and/or invade a host, so as to achieve the control of insect invasions and damages caused thereby.

In order to achieve the above-mentioned object, the present invention provides the following technical solutions.

In one aspect, the present invention provides an isolated polynucleotide, which is selected from:
(a) a polynucleotide sequence as shown in SEQ ID NO: 1; or
(b) a polynucleotide sequence of at least 15 consecutive nucleotides of SEQ ID NO: 1, wherein a double-stranded RNA comprising at least one strand complementary to the polynucleotide sequence, when ingested by an insect pest of *Coleoptera*, inhibits growth of the insect pest of *Coleoptera*; or
(c) a polynucleotide sequence of at least 17 consecutive nucleotides of SEQ ID NO: 1, wherein a double-stranded RNA comprising at least one strand complementary to the polynucleotide sequence, when ingested by an insect pest of *Coleoptera*, inhibits growth of the insect pest of *Coleoptera*; or
(d) a polynucleotide sequence of at least 19 consecutive nucleotides of SEQ ID NO: 1, wherein a double-stranded RNA comprising at least one strand complementary to the polynucleotide sequence, when ingested by an insect pest of *Coleoptera*, inhibits growth of the insect pest of *Coleoptera*; or
(e) a polynucleotide sequence of at least 21 consecutive nucleotides of SEQ ID NO: 1, wherein a double-stranded RNA comprising at least one strand complementary to the polynucleotide sequence, when ingested by an insect pest of *Coleoptera*, inhibits growth of the insect pest of *Coleoptera*; or
(f) any one of the polynucleotide sequences as shown in SEQ ID NO: 3 to SEQ ID NO: 6; or
(g) a polynucleotide sequence that is hybridized with or complementary to the polynucleotide sequence as defined in any one of the above-mentioned (a) to (f) under stringent conditions.

Preferably, the polynucleotide also comprises a complementary sequence of the polynucleotide sequence.

More preferably, the polynucleotide sequence also comprises a spacer sequence.

Most preferably, the spacer sequence is SEQ ID NO: 9.

Based on the above-mentioned technical solutions, the insect pest of *Coleoptera* is *Monolepta hieroglyphica* (Motschulsky).

In another aspect, the present invention provides an expression cassette, comprising the polynucleotide sequence under regulation of an effectively linked regulatory sequence.

In another aspect, the present invention provides a recombinant vector comprising the polynucleotide sequence or the expression cassette.

In another aspect, the present invention also provides use of the polynucleotide sequence for interfering with expression of a target sequence in an insect pest of *Coleoptera* or inhibiting growth of the insect pest of *Coleoptera*.

In another aspect, the present invention also provides an interfering ribonucleic acid, wherein the interfering ribonucleic acid acts to down-regulate expression of at least one target gene in an insect pest of *Coleoptera* after being ingested by the insect pest, wherein the interfering ribonucleic acid comprises at least one silencing element, wherein the silencing element is a double-stranded RNA region comprising complementary strands which have been annealed, and one strand of which comprises or consists of a nucleotide sequence at least partially complementary to a target sequence within the target gene, and the target gene comprises the polynucleotide sequence.

Preferably, the silencing element comprises or consists of a sequence of at least 15 consecutive nucleotides complementary to or at least partially complementary to a target fragment within the target sequence.

Preferably, the silencing element comprises or consists of a sequence of at least 17 consecutive nucleotides complementary to or at least partially complementary to a target fragment within the target sequence.

Preferably, the silencing element comprises or consists of a sequence of at least 19 consecutive nucleotides complementary to or at least partially complementary to a target fragment within the target sequence.

Preferably, the silencing element comprises or consists of a sequence of at least 21 consecutive nucleotides complementary to or at least partially complementary to a target fragment within the target sequence.

Optionally, the interfering ribonucleic acid comprises at least two silencing elements, each of which comprises or consists of a nucleotide sequence at least partially complementary to a target sequence within the target gene.

Preferably, each of the silencing elements comprises or consists of a different nucleotide sequence complementary to a different target sequence.

More preferably, the different target sequence is derived from a single target gene or from a target gene different from the target gene.

Further preferably, the target gene different from the target gene is derived from a same insect pest of *Coleoptera* or a different insect pest of *Coleoptera*.

Most preferably, the insect pest of *Coleoptera* is *Monolepta hieroglyphica* (Motschulsky).

Based on the above-mentioned technical solutions, the interfering ribonucleic acid also comprises a spacer sequence.

Particularly, the spacer sequence is SEQ ID NO: 9.

In another aspect, the present invention also provides a composition for controlling invasion of an insect pest of *Coleoptera*, comprising at least one of the interfering ribonucleic acids and at least one suitable carrier, excipient or diluent.

Preferably, the composition comprises a host cell expressing or capable of expressing the interfering ribonucleic acid. Particularly, the host cell is a bacterial cell.

More preferably, the composition is a solid, a liquid or a gel. Particularly, the composition is an insecticidal spray.

Optionally, the composition also comprises at least one pesticide, wherein the pesticide is a chemical pesticide, a potato tuber-specific protein, a *Bacillus thuringiensis* insecticidal protein, a *Xenorhabdus ehlersii* insecticidal protein, a *Photorhabdus* insecticidal protein, a *Bacillus laterosporus* insecticidal protein or a *Bacillus sphaericus* insecticidal protein.

In another aspect, the present invention also provides use of the composition for controlling invasion of an insect pest of *Coleoptera* for preventing and/or controlling invasion of an insect pest of *Coleoptera*.

Preferably, the insect pest of *Coleoptera* is *Monolepta hieroglyphica* (Motschulsky).

In another aspect, the present invention also provides a method for controlling invasion of an insect pest of *Coleoptera*, comprising contacting the insect pest of *Coleoptera* with an effective amount of at least one of the interfering ribonucleic acid sequences.

In another aspect, the present invention also provides a method for increasing plant resistance to an insect pest of *Coleoptera*, comprising introducing the polynucleotide, the expression cassette, the recombinant vector, or a construct comprising the interfering ribonucleic acid, into the plant.

In another aspect, the present invention also provides a method for producing a plant capable of controlling an insect pest of *Coleoptera*, comprising introducing the polynucleotide, the expression cassette, the recombinant vector, or a construct comprising the interfering ribonucleic acid, into the plant.

In another aspect, the present invention also provides a method for protecting a plant from damage caused by an insect pest of *Coleoptera*, comprising introducing the polynucleotide, the expression cassette, the recombinant vector, or a construct comprising the interfering ribonucleic acid, into the plant, wherein when ingested by the insect pest of *Coleoptera*, the plant being introduced acts to inhibit growth of the insect pest of *Coleoptera*.

Based on the above-mentioned technical solutions, the plant is soybean, wheat, barley, maize, tobacco, rice, rape, cotton or sunflowers.

The present invention comprises a method for regulating or inhibiting the expression of one or more target genes in an insect pest of *Coleoptera*, the method comprising: introducing part or all of a stabilized double-stranded RNA (such as dsRNA) or a modified form thereof (for example, a small interfering RNA sequence) into a cell of an invertebrate harmful insect or an extracellular environment thereof. In the insect body, the dsRNA or siRNA enters the cell, inhibits the expression of at least one or more target genes, and such an inhibition results in the weakening of the abilities of the insect to survive, grow, reproduce and invade a host.

The present invention provides an isolated and purified polynucleotide having a sequence as shown in SEQ ID NO: 1. The present invention also provides any RNA expressed by the polynucleotide, including dsRNA. The present invention further provides a stabilized double-stranded RNA molecule for inhibiting the expression of a target sequence in a pest of *Coleoptera*. The stabilized double-stranded RNA comprises at least two coding sequences, which are arranged in the sense and antisense directions relative to at least one promoter, wherein the nucleotide sequences comprising a sense strand and an antisense strand are connected or linked via a spacer sequence of at least about 5 to 1,000 nucleotides, wherein the sense strand and antisense strand can be of different lengths, and wherein at least one of the two coding sequences has at least 80%, at least 90%, at least 95%, at least 98%, or 100% sequence identity to any nucleotide sequence shown in SEQ ID NO: 1.

When being expressed as a dsRNA and administrated to a pest, the fragment can be defined as one resulting in death, and inhibited, hindered or halted feeding activity of the pest. The fragment can, for example, comprise at least about 19, 21, 23, 25, 40, 60, 80, 100, 125 or more consecutive nucleotides or about 19 to about 100 nucleotides, or more, of any one or more sequences of SEQ ID NO: 1 or the complementary sequences thereof, such as SEQ ID NO: 3 to SEQ ID NO: 6. Particularly useful is a dsRNA sequence comprising about 19 to 300 nucleotides homologous to the target sequence of pest. The present invention also provides a RNA expressed by any of the polynucleotide sequences, including dsRNA. A sequence selected for expressing a gene inhibitor and for expressing a RNA inhibiting a single gene or gene family in one or more target pests can be constructed using a single sequence from one or more target pests, or the DNA sequence can be constructed as a chimera from a variety of DNA sequences.

The plant in the present invention can include any propagation or reproduction material of a plant, and can also include a plant cell, a plant protoplast, a plant tissue culture, a plant callus and an intact plant cell in a plant or portions thereof, with these plant portions being, for example, embryos, pollen, ovules, seeds, leaves, flowers, branches, fruits, kernels, ears, cobs, husks, stalks, roots, or root tips.

The *Monolepta hieroglyphica* (Motschulsky) in the present invention is a holometabolous insect of Galeruca, belonging to the Chrysomelidae family of *Coleoptera*. Its eggs, larvae and pupae live in the soil, and the adults after emergence will fly out of the soil. It occurs one generation per year and passes the winter as diapause eggs, which are started to be hatched in May each year; larvae may be observed in the field soil from May to early July; pupae may often be seen in the field from late-June to mid-July; adults after emergence are occasionally flying into the fields of corn, soybeans or other plants to cause damage in mid-July; the peak period of emergence is from late-July to early August. The adult insects will be ready to lay eggs about 15 days after emergence. The egg-laying period lasts for about 1 month.

The larvae of *Monolepta hieroglyphica* (Motschulsky) feed mainly on the roots of crops in the farm field, and thus the damage caused thereby cannot be seen above the ground; it can be found in mid-July each year that their adults are damaging the leaves in corn and soybean fields; from late-July to early August a large number of adults are damaging the corn silk by biting off the corn silk and severely impairing pollination, resulting in pointed and spindle-shaped ears, and thus lower corn yield. Subsequently, the *Monolepta hieroglyphica* (Motschulsky) adults will migrate to soybean fields to eat soybean leaves or to the surrounding vegetable fields to damage the vegetables. The damage area of corn caused by *Monolepta hieroglyphica* (Motschulsky) from 2009 to 2016 in China had been doubled from 16 million mu (i.e., about 1.07 million hectare) to 40 million mu (i.e., about 2.67 million hectare), and the damage regions had been expanded from the Northwest to the major corn-growing areas such as Northeast and Northern parts of China.

In the meantime, with the continuous advancement of straw return-to-field measures, field humus and substances covering the soil surface have been increasingly enriched and accumulated, and thus it is more difficult to apply pesticides to the soil and the control of *Monolepta hieroglyphica* (Motschulsky) also becomes trickier. In other words, straw return-to-field, which furnishes a natural shelter for the *Monolepta hieroglyphica* (Motschulsky) larvae, may lead to a much higher survival rate of *Monolepta hieroglyphica* (Motschulsky) larvae, thereby resulting in higher population density of the *Monolepta hieroglyphica* (Motschulsky) insects. The *Monolepta hieroglyphica* (Motschulsky) adults, as the insects which can skillfully fly and jump, will start to damage the corn in the mid- to late-July after emergence when the corn is growing at silking stage. In this case, the corn has grown to certain height; and the application of pesticides becomes more difficult and is likely to cause a sad tragedy of accidentally hurting a person who is applying them. Also, the non-selective insecticidal effect can cause damage to crops and non-target organisms. Moreover, chemical pesticides may have a cumulative effect in the human body to become mutagens or carcinogens. Therefore, there is a need to find a precise and environmentally friendly method that can be simply and easily operated by a farmer to control the damage caused by *Monolepta hieroglyphica* (Motschulsky). By using genetic modification, the crops can have certain insecticidal efficacy against the pests over the entire growing period, and the entire plants are protected during their whole growing period. To address the above problems, the best solution is to adopt a method of controlling *Monolepta hieroglyphica* (Motschulsky) by using genetically modified RNAi means so as to provide the corn with complete-control over the entire plants during the whole growing period.

The expression "controlling an insect" or "controlling a pest" or "controlling an insect pest" in the present invention means any effect on an insect which can result in limitation of the damage caused by the insect, including, but not limited to, killing the insect, inhibiting development of the insect, changing fertility or growth of the insect in such a manner that the insect can only cause less damage to the plant, reducing the quantity of progenies generated by the insect, producing less normal insects, producing insects which will be more easily attacked by predators or preventing the insects from eating the plants.

The expression "target gene" in the present invention means any sequence intended to be down-regulated in an insect. Insect infestations are controlled by down-regulating the target gene, for example by disrupting necessary biological processes in the insects. Therefore, preferred target genes include, but are not limited to, genes playing essential roles in regulating feeding activity, survival, growth, development, reproduction, invasion and infection. When the expression of the target gene is down-regulated or inhibited, at least 30% of the insects are killed; or the growth of at least 30% of the insects is prevented/slowed/hindered/delayed/blocked, the reproduction of at least 30% of the insects is prevented, and the change in at least 30% of the insects through their life cycle is prevented; or the damage caused by the insects and/or the abilities of the insects to infect or infest the environment, surface and/or plants or crop species is decreased; or at least 30% of the insects are stopped feeding from natural food sources thereof (such as a plant and a plant product). These target genes can be expressed in all or a portion of insect cells. Additionally, these target genes can be only expressed in a specific stage in a life cycle of the insects, for example in the adult stage, larval phase or egg stage.

In the present invention, the term "pest" is preferably an insect causing plant invasion/infestation/infections, and belongs to *Coleoptera*, preferably *Monolepta hieroglyphica* (Motschulsky). The terms "infestation", "infection" and/or "invasion" can be generally used interchangeably throughout the document.

The term "RNA interference (RNAi)" in the present invention means some RNAs that can high efficiently and specifically block the expression of a specific gene in vivo, promote the degradation of mRNA, and induce a cell to exhibit a specific gene deletion phenotype; this technology is also referred to as RNA intervention or interference. RNA interference is a highly specific gene silencing mechanism at the mRNA level.

The term "nucleic acid" in the present invention means a single-stranded or double-stranded polymer of deoxyribonucleic acid or ribonucleic acid bases read from the 5'-terminus to 3'-terminus. Optionally, the term "nucleic acid" can also comprise non-naturally occurring or changed bases which allow correct reading by a polymerase and will not reduce the expression of a polypeptide encoded by the nucleic acid. The term "nucleotide sequence" means a sense strand and an antisense strand of a nucleic acid present as individual single strands or present in a dimer. The term "ribonucleic acid" (RNA) includes RNAi (RNA interference), dsRNA (double-stranded RNA), siRNA (small interfering RNA), mRNA (messenger RNA), miRNA (microRNA), tRNA (transfer RNA charged with or without corresponding acylated amino acids) and cDNA and genomic DNA, as well as DNA-RNA hybrids. The term "nucleic acid fragment", "nucleic acid sequence fragment" or the more commonly-known term "fragment" will be understood by a person skilled in the art to include a genomic sequence, a ribosomal RNA sequence, a transfer RNA sequence, a messenger RNA sequence, an operon sequence and a smaller engineered nucleotide sequence, wherein these sequences express or can be engineered to express a protein, a polypeptide or a peptide.

The term "interfering ribonucleic acid" in the present invention covers any type of RNA molecule capable of down-regulating or "silencing" the expression of a target sequence, including, but not limited to, sense RNA, antisense RNA, siRNA, miRNA, dsRNA, hairpin RNA (hpRNA), and the like. Methods for measuring functional interfering RNA molecules are well known in the art and have been disclosed.

The interfering ribonucleic acid in the present invention achieves specific down-regulation of the expression of a target gene by binding to a target sequence within the target gene. The reason for the occurrence of the binding is the base pairing between the complementary regions of the interfering RNA and the target sequence.

The present invention encompasses nucleic acid molecules or fragments thereof that are hybridized (in particular specifically hybridized) with the polynucleotide according to the present invention under "stringent condition". As known to the person skilled in the art, nucleic acid molecules or fragments thereof are capable of specifically hybridizing with other nucleic acid molecules under certain conditions. In the present invention, if two nucleic acid molecules can form an antiparallel nucleic acid structure with double strands, it can be determined that these two molecules can hybridize with each other specifically. If two nucleic acid molecules are completely complementary, one of the two molecules is called as the "complement" of the other one. In this invention, when every nucleotide of a nucleic acid molecule is complementary to the corresponding nucleotide of another nucleic acid molecule, it is identified that the two molecules are "completely complementary". If two nucleic acid molecules can hybridize with each other with enough stability so that they can anneal to and bind to each other under at least normal "low-stringent" conditions, these two nucleic acids are identified as "minimum complementary". Similarly, if two nucleic acid molecules can hybridize with each other with enough stability so that they can anneal to and bind to each other under normal "high-stringent" conditions, it is identified that these two nucleic acids are "complementary". Deviation from "completely complementary" can be allowed, as long as the deviation does not completely prevent the two molecules to form a double-strand structure. A nucleic acid molecule which can be taken as a primer or a probe must have sufficiently complementary sequences to form a stable double-strand structure in the specific solvent at a specific salt concentration. In the present invention, basically homologous sequence refers to a nucleic acid molecule, which can specifically hybridize with the complementary strand of another matched nucleic acid molecule under "high-stringent" conditions. The stringent conditions for DNA hybridization are well-known to those skilled in the art, such as treatment with 6.0×sodium chloride/sodium citrate (SSC) solution at about 45° C. and washing with 2.0×SSC at 50° C. For example, the salt concentration in the washing step is selected from 2.0×SSC and 50° C. for the "low-stringent" conditions and 0.2×SSC and 50° C. for the "high-stringent" conditions. In addition, the temperature in the washing step ranges from about 22°

C. for the "low-stringent" conditions to about 65° C. for the "high-stringent" conditions. Both temperature and the salt concentration can vary together, or one of them can remain unchanged while the other variable changes. Preferably, the polynucleotide of this invention is specifically hybridized in 6.0×SSC and 0.5% SDS solution at 65° C. for the "high-stringent" conditions; then the membrane was washed once in 2×SSC and 0.1% SDS solution and in 1×SSC and 0.1% SDS solution, respectively.

The term "silencing element" refers to a part or region of an interfering ribonucleic acid comprising or consisting of a nucleotide sequence complementary to or at least partially complementary to a target sequence within a target gene, wherein the part or region acts as an active part of the interfering ribonucleic acid so as to direct the down-regulation of the expression of the target gene. The silencing element comprises a sequence having at least 15 consecutive nucleotides, preferably at least 18 or 19 consecutive nucleotides, more preferably at least 21 consecutive nucleotides, and even more preferably at least 22, 23, 24 or 25 consecutive nucleotides complementary to a target sequence within a target gene; or an interfering ribonucleic acid consisting thereof.

The term "expression of a target gene" in the present invention refers to the transcription and accumulation of RNA transcripts encoded by a target gene and/or translation of mRNA into a protein.

The term "down-regulation" refers to any of the methods known in the art by which an interfering ribonucleic acid reduces the level of primary RNA transcript, mRNA or protein produced from a target gene. The down-regulation refers to a situation whereby the level of RNA or proteins produced from a gene is reduced by at least 10%, preferably at least 33%, more preferably at least 50%, and even more preferably at least 80%. Specifically, down-regulation refers to the reduction of the level of RNA or proteins produced from a gene in an insect cell by at least 80%, preferably at least 90%, more preferably at least 95%, and most preferably at least 99%, as compared with a suitably controlled insect (for example, an insect which has not been exposed to the interfering ribonucleic acid or has been exposed to a control interfering ribonucleic acid). Methods for detecting the reduction of RNA or protein levels are well known in the art, and include RNA solution hybridization, Northern hybridization, reverse transcription (for example quantitative RT-PCR analysis), microarray analysis, antibody binding, enzyme-linked immunosorbent assay (ELISA) and Western blotting. Meanwhile, down-regulation can also mean that, as compared with the suitable insect control, the level of RNA or proteins is reduced to a level sufficient to result in the insect phenotype generating a detectable change, for example cell death, growth cessation, and the like. Therefore, down-regulation can be measured by phenotype analysis of the insect using conventional techniques in the art.

The expression "inhibition of expression of a target gene" in the present invention refers to the reduction or absence (below a detectable threshold) of the level of the proteins and/or mRNA product of the target gene. Specificity refers to an ability to inhibit a target gene and produce no effect on other genes in a cell, and brings about no effect on any gene in a cell generating dsRNA molecules.

The "sense" RNA in the present invention refers to an RNA transcript corresponding to a sequence or fragment present in the form of mRNA which can be translated into a protein by a plant cell. The "antisense" RNA in the present invention refers to RNA complementary to all or part of mRNA produced normally in a plant. The complementation of an antisense RNA can be directed at any part of a transcript of a specific gene, i.e. a 5' non-coding sequence, 3' non-coding sequence, intron or coding sequence. The term "RNA transcript" in the present invention refers to a product obtained by transcription catalyzed by an RNA polymerase performed on the DNA sequence. When the RNA transcript is a completely complementary copy of a DNA sequence, the RNA transcript is referred to as a primary transcript, or is an RNA obtained by post-transcriptional processing of the primary transcript, which is referred to as a mature RNA.

The interfering ribonucleic acid in the present invention down-regulates the expression of a gene by RNA interference or RNAi. RNAi is a typical method for sequence-specific gene regulation mediated by a double-stranded RNA molecule (such as siRNA). siRNA comprises a sense RNA strand being annealed with an antisense RNA strand by complementary base pairing. The sense strand or "leading strand" in a siRNA molecule comprises a nucleotide sequence complementary to a nucleotide sequence located within an RNA transcript of a target gene. Therefore, the sense strand of siRNA can be annealed with the RNA transcript by Waston-Crick-type base pairing, and targets the RNA so that the RNA is degraded in a cellular complex referred to as RNAi induced silencing complex or RISC. In the case of a preferred interfering ribonucleic acid in the present invention, the silencing element can be a double-stranded region comprising complementary strands being annealed, at least one strand of which comprises a nucleotide sequence complementary or at least partially complementary to a target sequence within a target gene; or comprises an interfering ribonucleic acid consisting thereof. The double-stranded region has a length of at least about 15 to about 25 base pairs, or a length of about 25 to about 100 base pairs, or even a length of about 3,000 base pairs.

The dsRNA molecule in the present invention can serve as a precursor for active siRNA molecules which direct RNA transcripts to the RISC complex for subsequent degradation. A dsRNA molecule present in an organism or the cellular surroundings thereof can be ingested by the organism and processed by an enzyme known as DICER to obtain a siRNA molecule. Optionally, a dsRNA molecule can be produced in vivo, i.e., one or more polynucleotides encoding the dsRNA present in a cell (for example, a bacterial cell or a plant cell) are transcribed, and processed by DICER in a host cell or preferably in an insect cell after ingesting a longer precursor dsRNA. The dsRNA can be formed by two separate (sense and antisense) RNA strands being annealed by complementary base pairing. Alternatively, dsRNA can be a single strand, which can refold itself to form a hairpin RNA or a stem-loop structure. In the case of one single RNA, the double-stranded region or "stem" is formed of two regions or segments of the RNA, wherein these regions or segments are substantially inverted repeat sequences for each other, and have sufficient complementarity to allow the formation of a double-stranded region. One or more functional double-stranded silencing elements can be present in this "stem region" of the molecule. Inverted repeat regions are typically spaced via a region or segment referred to as a "loop" region in an RNA. This region can comprise any nucleotide sequence which confers sufficient flexibility to allow self-pairing between flanking complementary regions of RNA, and in general, the loop region is substantively single stranded and serves as a spacer sequence between inverted repeat sequences.

The interfering ribonucleic acid in the present invention comprises at least one double-stranded region, typically a silencing element of the interfering ribonucleic acid, which comprises a sense RNA strand being annealed with an antisense RNA strand by complementary base pairing, wherein the sense strand of the dsRNA molecule comprises a nucleotide sequence complementary to a nucleotide sequence located within the RNA transcript of a target gene. The silencing element or at least one strand thereof (when the silencing element is double stranded) can be completely or partially complementary to a target sequence of a target gene. The term "completely complementary" means that all the bases of the nucleotide sequence of a silencing element are complementary to or "match" the bases of a target sequence. The term "at least partially complementary" refers to less than 100% of matching degree being present between the bases of a silencing element and the bases of a target sequence. A person skilled in the art would understand that in order to mediate the down-regulation of the expression of a target gene, the silencing element only needs to be at least partially complementary to the target sequence. It is known in the art that a RNA sequence having an insertion, deletion and mismatch with respect to the target gene can still be effective in terms of RNAi. Preferably, the silencing element and the target sequence of the target gene share at least 80% or 85% sequence identity, preferably at least 90% or 95% sequence identity, or more preferably at least 97% or 98% sequence identity, and still more preferably at least 99% sequence identity. Optionally, over each length of 24 partially complementary nucleotides, as compared with the target sequence, the silencing element can comprise 1, 2 or 3 mismatches. It is well known to a person skilled in the art that the complementarity degree shared between the silencing element and the target sequence varies with the expression of the target gene to be down-regulated or the insect species to be controlled.

The target sequence in the present invention can be selected from any suitable region or nucleotide sequence of a target gene or an RNA transcript thereof. For example, the target sequence can be located within the 5' UTR or 3' UTR of the target gene or RNA transcript, or within an extron or intron region of the gene.

The interfering ribonucleic acid in the present invention can comprise one or more silencing elements, wherein each silencing element comprises or consists of a nucleotide sequence at least partially complementary to a target sequence within a target gene, and functions to down-regulate the expression of the target gene after being ingested by an insect. The term "a plurality of" or "more" means at least two, at least three, at least four, and so on until at least 10, 15, 20 or at least 30. The interfering ribonucleic acid comprises a plurality of copies of a single silencing element, i.e., repeats of the silencing element binding to a specific target sequence within a specific target gene. The silencing element within the interfering ribonucleic acid can also comprise or consist of different nucleotide sequences complementary to different target sequences. It shall be apparent that a combination of a plurality of copies of the same silencing element and a silencing element binding to a different target sequence also falls within the scope of the present invention.

In the present invention, in order to achieve the down-regulation of a specific target gene in an insect from *Coleoptera*, different target sequences can be derived from a single target gene in an insect. In this case, silencing elements in an interfering ribonucleic acid can be combined according to the original order of target sequences present in a target gene, or as compared with the order of the target sequences in the target gene, the silencing elements can be disorganized and randomly combined in any rank order in an environment of the interfering ribonucleic acid.

Optionally, different target sequences represent a single target gene respectively, but are derived from different insect species.

Optionally, different target sequences can be derived from different target genes. If an interfering ribonucleic acid is used for preventing and/or controlling pest invasions, then it is preferred that different target sequences are selected from the group consisting of genes regulating necessary biological functions of an insect, wherein these biological functions include, but are not limited to, survival, growth, development, reproduction and pathogenicity. The target sequences can regulate the same or different biological pathways or processes.

In the present invention, different genes targeted by different silencing elements can be derived from the same insect. This method can be used for achieving an enhanced attack against a single insect. Particularly, different target genes can be differentially expressed in different stages of life cycle of the insect, for example the mature adult stage, immature larval stage and egg stage. Therefore, the interfering ribonucleic acid in the present invention can be used for preventing and/or controlling insect invasions in one or more stages of the life cycle of the insect. Alternatively, different genes targeted by different silencing elements are derived from different insects; therefore, the interfering ribonucleic acid in the present invention can also be used for simultaneously preventing and/or controlling invasions of one or more types of insects.

The silencing element in the present invention can be a consecutive region of an interfering ribonucleic acid or can be spaced apart via a linker sequence. The linker sequence can comprise a short random nucleotide sequence that is not complementary to any target sequence or target gene. The linker sequence can be a conditional self-cleavage RNA sequence, preferably a pH sensitive linker or a hydrophobic sensitive linker. The linker can also comprise a nucleotide sequence equivalent to an intron sequence. The length of the linker sequence can be in a range of 1 base pair to about 10,000 base pairs, provided that the linker will not weaken the ability of the interfering ribonucleic acid to down-regulate the gene expression.

In addition to one or more silencing elements and any linker sequence, the interfering ribonucleic acid in the present invention can also comprise at least one additional polynucleotide sequence. The additional polynucleotide sequence is selected from: (1) a sequence capable of protecting the interfering ribonucleic acid from RNA processing; (2) a sequence affecting the stability of the interfering ribonucleic acid; (3) a sequence which allows binding of a protein to facilitate the ingestion of the interfering ribonucleic acid by an insect cell; (4) a sequence facilitating the large-scale production of the interfering ribonucleic acid; (5) an aptamer sequence capable of binding to an receptor or binding to a molecule on surface of an insect cell so as to facilitate the ingestion; or (6) a sequence catalyzing the processing of the interfering ribonucleic acid in an insect cell and thereby enhancing the efficacy of the interfering ribonucleic acid.

The length of the interfering ribonucleic acid in the present invention needs to be sufficient to be ingested by an insect cell and down-regulate a target gene in the insect. The upper limit of the length can depend on: (1) the requirement for ingestion of the interfering ribonucleic acid by an insect cell, and (2) the requirement of the interfering ribonucleic acid in the insect cell being processed to mediate gene silence through an RNAi approach, and the length can also be specified by a method of production and a formulation for delivering the interfering ribonucleic acid to the cell. Preferably, the length of the interfering ribonucleic acid in the present invention will be between 19 and 10,000 nucleotides, preferably between 50 and 5,000 nucleotides or between 100 and 2,500 nucleotides, more preferably having a length between 80 and 2,000 nucleotides.

The interfering ribonucleic acid in the present invention can comprise DNA bases, unnatural bases or an unnatural backbone connection or modifications of a sugar-phosphate backbone, for example, for enhancing the stability during storage or enhancing the resistance to nuclease degradation. Additionally, the interfering ribonucleic acid can be produced chemically or enzymatically through a manual or automatic reaction by a person skilled in the art. Optionally, the interfering ribonucleic acid can be transcribed from a polynucleotide encoding thereof. Therefore, the present invention provides an isolated polynucleotide for encoding any one of the interfering ribonucleic acid.

The polynucleotide in the present invention can be inserted into a DNA construct or a vector known in the art by a conventional molecular cloning technique. The DNA construct can be a recombinant DNA vector, for example, a bacterial, viral or yeast vector. The DNA construct is an expression construct, in which the polynucleotide is operably linked to at least one regulatory sequence capable of driving the expression of the polynucleotide sequence. The term "regulatory sequence" refers to any nucleotide sequence capable of affecting the expression of an operably linked polynucleotide, including, but not limited to, a promoter, an enhancer, and other naturally generated or synthesized transcriptional activation elements. The regulatory sequence can be located at the 5' or 3' terminus of the polynucleotide sequence. The term "operably linked" refers to a functional connection between a regulatory sequence and a polynucleotide sequence, in which the connection makes the regulatory sequence drive the expression of the polynucleotide. Operably linked elements can be consecutive or inconsecutive.

The regulatory sequence in the present invention can be a promoter. Preferably, the promoter is a plant expressible promoter. The "plant expressible promoter" refers to a promoter that ensures the expression of the polynucleotide linked thereto in a plant cell. The plant expressible promoter can be a constitutive promoter. Examples of promoters directing the constitutive expression in plants include, but are not limited to, a 35S promoter derived from cauliflower mosaic virus, maize ubi promoters, rice GOS2 gene promoters, and the like. Alternatively, the plant expressible promoter can be a tissue specific promoter, i.e. the promoter directs the expression of an coding sequence in several tissues, such as green tissues, at a level higher than in other tissues of the plant (which can be measured through conventional RNA trials), such as a PEP carboxylase promoter. Alternatively, the plant expressible promoter can be a wound-inducible promoter. The wound-inducible promoter or a promoter directing the expression mode induced by the wound means that when a plant suffers from a wound caused by a mechanical factor or the gnawing of insects, the expression of the polynucleotide under the regulation of the promoter is significantly improved than when under normal growth conditions. Examples of the wound-inducible promoters include, but are not limited to, promoters of potato and tomato protease inhibitor genes (pinI and pinII) and maize protease inhibitor genes (MPI).

Optionally, one or more transcription termination sequences can be incorporated into the expression construct in the present invention. The term "transcription termination sequence" covers a control sequence at the terminus of a transcription unit, and sends signals regarding the transcription termination, 3' processing and polyadenylation of a primary transcript. The additional regulatory element includes, but is not limited to, a transcription or translation enhancer which can be incorporated into an expression construct, for example, a double enhancing CaMV35S promoter.

The method for producing any interfering ribonucleic acid in the present invention comprises the steps of: (1) contacting the polynucleotide encoding the interfering ribonucleic acid or a DNA construct comprising the polynucleotide with a cell-free component; and (2) introducing the polynucleotide encoding the interfering ribonucleic acid or the DNA construct comprising the polynucleotide (for example, through transformation, transfection or injection) into a cell.

In the present invention, a host cell comprising any interfering ribonucleic acid of the present invention, any polynucleotide of the present invention or a DNA construct comprising these polynucleotides can be a prokaryotic cell, including, but not limited to, Gram-positive and Gram-negative bacterial cells; or a eukaryotic cell, including, but are limited to, a yeast cell or a plant cell. Preferably, the host cell is a bacterial cell or a plant cell. The polynucleotide or DNA construct in the present invention can be present or maintained as an extrachromosomal element in the host cell, or can be stably incorporated into the genome of the host cell.

In the present invention, in the case of an interfering ribonucleic acid being expressed in a host cell and/or used for preventing and/or controlling insect infestations in a host organism, it is preferred that the interfering ribonucleic acid does not exhibit a significant "off-target" effect, i.e., the interfering ribonucleic acid does not affect the expression of a non-target gene in the host. Preferably, the silencing gene does not exhibit significant complementarity to a nucleotide sequence apart from a given target sequence of the target gene. The silencing element shows less than 30%, more preferably less than 20%, more preferably less than 10%, and even more preferably less than 5% sequence identity to any gene of the host cell or organism. If the genomic sequence data of the host organism is available, then the identity to the silencing element can be crosschecked using standard bioinformatics tools. Within a region having 17 consecutive nucleotides, more preferably within a region having 18 or 19 consecutive nucleotides, and most preferably within a region having 19 or 20 or 21 consecutive nucleotides, the silencing element and the gene from the host cell or organism do not have sequence identity.

In the present invention, the composition for preventing and/or controlling insect infestations comprises at least one interfering ribonucleic acid and optionally at least one suitable carrier, excipient or diluent, wherein the interfering ribonucleic acid functions to down-regulate the expression of a target gene in an insect after being ingested by the insect. The interfering ribonucleic acid comprises or consists of at least one silencing element, and the silencing element is a double-stranded RNA region containing complementary strands being annealed, one strand of which (sense strand) comprises a nucleotide sequence at least partially complementary to a target sequence within a target gene. The target gene includes, but is not limited to, genes regulating the survival, growth, development, reproduction and pathogenicity of an insect. Optionally, the composition comprises at least one host cell, and the host cell comprises at least one interfering ribonucleic acid or a DNA construct encoding the interfering ribonucleic acid, and optionally at least one suitable carrier, excipient or diluent, wherein the interfering ribonucleic acid functions to down-regulate the expression of a target gene in an insect after the host cell is ingested by the insect.

The composition of the present invention can be presented as any suitable physical form to be applied to an insect. For example, the composition can be in the form of a solid (powder, pellet or bait), a liquid (including an insecticidal spray) or a gel. The composition can be a coating, paste or powder, which can be applied to a substrate so as to protect the substrate from the insect infestation. The composition can be used for protecting any substrate or material sensitive to the insect invasions or damage caused by the insect.

The properties of the excipient and the physical form of the composition can vary due to the properties of the substrate which is desired to be treated. For example, the composition can be a liquid which is brushed or sprayed onto a material or substrate to be treated or printed onto a material or substrate to be treated; or a coating or powder which is applied to a material or substrate to be treated.

In the present invention, the composition can be in the form of bait. The bait is used to induce an insect to be contacted with the composition. After being in contact with the insect, the composition is subsequently internalized by the insect through, for example, ingestion and mediates RNAi, thereby killing the insect. The bait can comprise a type of food, such as a type of protein-based food, for example fish meal. Boric acid can also be used as bait. The bait can depend upon the species to be targeted. An attractant can also be used, which, for example, can be a pheromone such as a male or female pheromone. The attractant can act to induce the contact between the insect and the composition, and can be targeted at a specific insect or can attract insects over the whole range, increasing the contact chance of the induced insects and the composition of the present invention, thereby achieving the purpose of killing a mass of insects. The bait can be in any suitable form, such as the form of a solid, a paste, a pellet or a powder.

The bait can also be taken by an insect to the insect community. The bait can then serve as a food source of other members in the community, thereby providing an effective control for a mass of insects and potentially the whole insect community. The bait can also be provided in a suitable "shell" or "trapper".

Additionally, the composition in contact with the insects can be held on the surface of the insects. Upon cleaning, whether cleaning a single insect on its own or cleaning each other, the composition can be ingested and can thus mediate the effect thereof in the insects. For this, the composition needs to be sufficiently stable, so that even when exposed to external environment conditions for a period of time (for example, several days), the interfering ribonucleic acid still remains intact and can mediate RNAi.

The composition in the present invention can be provided in the form of a spray. Therefore, a human user can directly spray the insects with the composition. The composition is then internalized by an insect, and can mediate RNA interference in the insect body, thereby controlling the insect. The spray is preferably a pressurized/atomized spray or a pump spray. These particles can have a suitable size so that they can be adhered to the insect, for example, adhered to the exoskeleton where the particles can be absorbed.

In the present invention, the carrier of the composition is an electrostatic powder or particle, which can be adhered to an insect. Optionally, the carrier of the composition can comprise magnetic particles, which can be adhered to the surface of the insect. Optionally, the carrier of the composition comprises metal particles, which are initially unmagnetized, but can become magnetically polarized upon entering an electric field provided by the insect body. Preferably, the composition is incorporated into a carrier which increases the ingestion of an interfering RNA by the insect. Such a carrier can be a lipid-based carrier, preferably including one or more of the following: an oil-in-water type emulsion, a micelle, cholesterol, lipopolyamine and liposome. Other agents improving the ingestion of the construct of the present invention are well known to a person skilled in the art, and include polycations, dextran and cationic lipids such as CS096 and CS102. Optionally, the carrier of the composition is a coagulant for nucleic acid, and preferred coagulant comprises spermidine or protamine sulfate, or derivatives thereof.

In the case that the composition of the present invention is suitable for preventing and/or controlling insect invasions in a plant, the composition can comprise an agriculturally suitable carrier. Such a carrier can be any material which can be tolerated by a plant to be treated, and the material would not cause inappropriate damage to the environment or other organisms therein, and allows the efficacy of the interfering ribonucleic acid on the insect to be maintained. In particular, the composition of the present invention can be formulated in accordance with the conventional agricultural practice used in the industry of biological pesticides, so as to be delivered to a plant. The composition can comprise an additional component capable of performing other functions, wherein these functions include, but are not limited to, (1) enhancing or improving the ingestion of the interfering ribonucleic acid by an insect cell, and (2) stabilizing the active components of the composition. Such additional component contained in the composition comprising the interfering ribonucleic acid can be a yeast tRNA or yeast total RNA.

The composition can be formulated for direct application or formulated as a concentrated form of a primary composition which needs to be diluted prior to use. Optionally, the composition can be provided in the form of a kit comprising the interfering ribonucleic acid or a host cell comprising/expressing the interfering ribonucleic acid in a container, and a suitable diluent or carrier for the RNA or host cell in a separate container. In the application of the present invention, the composition can be applied to a plant or any part thereof in any development stage of the plant, for example, during the culture of the plant in a field, the composition is applied to the aboveground part of the plant; or when the plant seeds are stored or after the plant seeds are sown in the soil, the composition is applied to the plant seeds. In general, it is important to achieve a good control over an insect in an early growth stage of the plant, since this stage is a period when the plant is possibly suffering from most serious insect damage.

In the present invention, the composition can be applied to the environment of insects through different techniques which include, but are not limited to, spraying, atomizing, dusting, scattering, pouring, seed coating, seed treatment, introduction into the soil and introduction into irrigation water. When a plant which is sensitive to insect infestations is treated, the composition can be delivered to the plant or a part thereof before the occurrence of the insect (for a preventative purpose) or after the emergence of signs of an insect invasion (for a control purpose).

The composition of the present invention can be formulated as comprising at least one additional active agent. Therefore, the composition can be provided in the form of a "multi-part kit", and the kit comprises a composition comprising an interfering ribonucleic acid in a container, and one or more suitable active components, such as chemical or biological pesticides, in a separate container. Optionally, the composition can be provided in the form of a mixture which is stable and the components of which can be used in combination with each other.

Suitable active components which can be used in a complementary manner with the interfering ribonucleic acid of the present invention include, but are not limited to, the following items: dursban, allethrin, resmethrin, tetrabromoethyl, dimethanol-cyclopropanecarboxylic acid (generally being comprised in a liquid composition); and hydramethylnon, avermectin, dursban, sulfluramid, hydroprene, fipronil (a GABA receptor), carbamic acid isopropyl phenyl methyl ester, indoxacarb, noviflumuron (a chitin synthesis inhibitor), imiprothrin, abamectin (a glutamate gated chloride ion channel), and imidacloprid (an acetylcholine receptor) (generally being comprised in a bait composition). Preferably, taking the health and environment into account, it is known that the active component is a pesticide such as hydramethylnon and avermectin.

The composition in the present invention can be formulated as comprising at least one additional agronomical reagent, such as a herbicide or an additional pesticide. The term "additional pesticide" or "a second pesticide" refers to a pesticide apart from the first or initial interfering RNA molecule of the composition. Optionally, the composition of the present invention can be delivered in combination with at least one additional agronomical reagent (for example a herbicide or a second pesticide). The composition can be provided in combination with a herbicide which is selected from any herbicide known in the art, for example, glyphosate, 2,4-D, imidazolinone, sulfonylurea and bromoxynil. The composition can also be provided in combination with at least one additional pesticide which can be selected from any pesticide known in the art and/or can comprise an interfering ribonucleic acid which functions to down-regulate the expression of a target gene in an insect after being ingested by the insect. The target pest is an insect and the interfering ribonucleic acid is selected from any one of the interfering ribonucleic acids in the present invention. The additional pesticide comprises an interfering ribonucleic acid which functions to down-regulate the expression of a known gene in any target pest. The initial interfering ribonucleic acid and the second or additional pesticide in the composition can be targeted at the same or different insects. For example, the initial interfering ribonucleic acid and the second pesticide can be targeted at different insects or can be targeted at insects of different families or classes, for example fungi or nematodes or insects. A person skilled in the art should be clear on how to detect a synergistic effect of the combination of the interfering ribonucleic acid and other agronomical reagents. Preferably, the composition comprises a first interfering ribonucleic acid and one or more additional pesticides, each of which has a toxicity for the same insect, wherein the one or more additional pesticides are selected from a potato tuber-specific protein, a *Bacillus thuringiensis* insecticidal protein, a *Xenorhabdus ehlersii* insecticidal protein, a *Photorhabdus* insecticidal protein, a *Bacillus laterosporus* insecticidal protein, a *Bacillus sphaericus* insecticidal protein and lignin. Different components can be delivered simultaneously or successively to a region or organism to be treated.

The method for preventing and/or controlling insect invasions in the present invention comprises contacting an insect with an effective amount of at least one interfering ribonucleic acid, wherein the interfering ribonucleic acid functions to down-regulate the expression of a necessary target gene of insect after being ingested by the insect. The necessary target gene can be any gene of the insect involved in the regulating of the initiation or maintenance of necessary biological processes required for infestation in the insect, and the biological processes include, but are not limited to, survival, growth, development, reproduction and pathogenicity.

The method for preventing and/or controlling insect invasions in the crop plant field in the present invention comprises expressing an effective amount of the interfering ribonucleic acid in the plant, and in the case that the method is used for controlling insect invasions, the term "effective amount" refers to an amount or concentration of the interfering ribonucleic acid required for producing a phenotypic effect on the insect, so that the number of the insects infesting a host organism is reduced and/or the amount of damage caused by the insect is decreased. The phenotypic effect can be insect death, and the use of the interfering RNA achieves an insect death rate of at least 20%, 30%, 40%, preferably at least 50%, 60%, 70%, and more preferably at least 80% or 90% as compared with a control insect. The phenotypic effect can also include, but is not limited to, the prevention of insect growth, arrest of feeding activity and reduction of egg-laying. Therefore, as compared with the control insect, the total number of the insects invading the host organism can be reduced by at least 20%, 30%, 40%, preferably by at least 50%, 60%, 70%, and more preferably by at least 80% or 90%. Optionally, as compared with the control insect, the damage caused by the insect can be reduced by at least 20%, 30%, 40%, preferably by at least 50%, 60%, 70%, and more preferably by at least 80% or 90%. Therefore, the present invention can be used to achieve at least 20%, 30%, 40%, preferably at least 50%, 60%, 70%, and more preferably at least 80% or 90% of control of the insect.

The method and composition in the present invention can be used to restrict or eliminate the invasion of a *Coleoptera* pest, preferably *Monolepta hieroglyphica* (Motschulsky), in the environment or on the surface where any pest host, pest symbiont or pest may be present, by providing one or more compositions comprising the dsRNA molecules in the present invention in the food of the pest. The method is especially beneficial for preventing the insect from attacking a plant, and the pest is defined as having a pH of about 4.5 to about 9.5, about 5 to about 9, about 6 to about 7 or about pH 7.0 in the digestive system.

The nucleotide sequence of the present invention can comprise inverted repeats spaced apart by a "spacer sequence". The spacer sequence can be a region comprising any of the following nucleotide sequences, if desired, which can promote the formation of a secondary structure between each segment of repeats. The spacer sequence is a part for a sense or antisense coding sequence of mRNA. Alternatively, the spacer sequence can comprise any combination of nucleotides or homologues thereof which can be covalently linked to a nucleic acid molecule. The spacer sequence can comprise a nucleotide sequence with a length of at least about 10-100 nucleotides, or a length of at least about 100-200 nucleotides, or a length of at least about 200-400 nucleotides, or a length of at least about 400-500 nucleotides.

In the present invention, the "introduction" of the interfering ribonucleic acid into a plant means introduction that can be performed by a direct transformation method, for example, *Agrobacterium*-mediated transformation for a plant tissue, microparticle bombardment, electroporation, etc.; or introduction that can be performed by hybridizing a plant having a heterogenous nucleotide sequence with another plant, so that the progenies have the nucleotide sequence incorporated into their genomes. Such breeding technologies are well known to a person skilled in the art.

The present invention provides a polynucleotide and method for controlling insect invasions, at least having the following advantages:

1. The present invention discloses, for the first time, a plurality of target sequences for controlling the target gene c46312 of an insect pest of Coleoptera, *Monolepta hieroglyphica* (Motschulsky), and furthermore, verifies that a nucleic acid inhibitor obtained based on these target sequences can be directly used for controlling invasions of insect pests from Coleoptera.

2. High species specificity. The target sequences disclosed herein for controlling an insect pest of Coleoptera, *Monolepta hieroglyphica* (Motschulsky), act with high specificity on *Monolepta hieroglyphica* (Motschulsky) and species that share close genetic affinities and have sequence identity.

3. Avoidance of development of resistance. The present invention does not rely on the binding of a specific dsRNA to a receptor protein in an insect body, and thus can effectively avoid the analogous risk of developing resistance to Bt-toxin proteins in the insect.

4. The RNAi technology used herein is highly efficient and specific, and the dsRNA obtained can be directly used in field for controlling the invasion of insect pests from Coleoptera, which is convenient, inexpensive in cost, and good in environment compatibility.

The technical solutions of the present invention are further described in details through drawings and examples below.

DETAILED DESCRIPTION

Figure 1:
FIG. 1 is an electrophoretogram showing the expression level of the target gene c46312 used in the polynucleotide and method for controlling insect invasions according to the present invention.

The technical solution of the polynucleotide and method for controlling insect invasions in the present invention is further illustrated by the specific examples below.

Example 1. Determination of Target Sequences of *Monolepta hieroglyphica* (Motschulsky)

1. Total RNA Extraction of *Monolepta hieroglyphica* (Motschulsky)

Newly-incubated instar larvae of *Monolepta hieroglyphica* (Motschulsky) were taken as materials, and RNA was extracted by using the conventional Trizol method, purified by a conventional method, and treated with a DNase, thereby obtaining a total RNA sample at a concentration of >300 ng/μL, a total amount of >6 μg, and $OD_{260/280}$ of 1.8-2.2.

2. Separation of mRNA and Synthesis of cDNA mRNA with polyA was separated from the total RNA sample prepared as above using magnetic beads with oligo-dT, and the first strand of cDNA was then synthesized using a random hexamer and a Superscript II reverse transcriptase kit of Invitrogen.

3. Screening of Target Genes

One target gene c46312 of *Monolepta hieroglyphica* (Motschulsky) was screened out from the genes that are in the larvae library with medium analytical expression value and may be involved in important metabolic pathways, and its full-length nucleotide sequence was shown in SEQ ID NO: 1, the amino acid sequence was shown in SEQ ID NO: 2.

4. Selection of Target Sequences within the Target Genes

Four target sequences with different ORF positions and/or different lengths of the target gene c46312 were selected, as shown in Table 1.

TABLE 1 sequence information of four target sequences

| Target sequence | Sequence number |
| --- | --- |
| c46312_g1-01 | SEQ ID NO: 3 |
| c46312_g1-02 | SEQ ID NO: 4 |
| c46312_g1-03 | SEQ ID NO: 5 |
| c46312_g1-04 | SEQ ID NO: 6 |

Example 2. Acquisition of dsRNA

The dsRNA of the above-mentioned four target sequences were synthesized respectively according to the instructions of MEGAscript RNAi Kit from ThermoFisher company, namely, c46312_g1-01 to c46312_g1-04; the size of the products were detected by agarose electrophoresis with a mass concentration of 1%, and the concentrations of c46312_g1-01 to c46312_g1-04 were determined respectively by NanoDrop 2000 (Thermo Scientific).

Example 3. Identification of the Ability of Controlling *Monolepta hieroglyphica* (Motschulsky) by Feeding dsRNA The isolated and purified c46312_g1-01 to c46312_g1-04 were mixed respectively and added evenly into feed at the ratios of 50 μg/g feed and 5 μg/g feed (Feed formula references Development of an artificial diet for the western corn rootworm, Entomologia Experimentalis et Applicata 105: 1-11, 2002.), to obtain c46312_g1-01-50 to c46312_g1-04-50 feed and c46312_g1-01-5 to c46312_g1-04-5 feed, respectively. In the control group, irrelevant dsRNA (SEQ ID NO: 15) was added to the feed CK, and other conditions were completely consistent. The newly-incubated larvae of *Monolepta hieroglyphica* (Motschulsky) were fed with the feed prepared as above. 30 newly-incubated larvae with an incubation time of not more than 24 hours were placed in each dish, in which the feed mixed with dsRNA was replaced every two days and fed until day 14. The insect mortality rate was counted every two days from the beginning of feeding, and the expression value of the target gene was determined on days 0, 4, 8, and 10 from the beginning of feeding, by using the specific methods as follows:

Step 301. The larvae, fed with c46312_g1-01-50 to c46312_g1-04-50 feed and c46312_g1-01-5 to c46312_g1-04-5 feed respectively, were collected on days 0, 4, 8, and 10, respectively, and frozen with liquid nitrogen;

Step 302. The total RNA of the above-mentioned larvae was extracted using the Trizol method, respectively;

Step 303. The cDNA was obtained by reverse transcription of the total RNA of the above-mentioned larvae using the whole gold kit (TransGen Biotech ER301-01), respectively.

Step 304. Ubiquitin-C was used as an internal reference gene for PCR amplification, and after amplification, 10 μL of the amplification product was taken for agarose gel electrophoresis with a mass concentration of 1%.

Five repeats were set for each treatment in the above-mentioned experiment, and the statistical results were shown in FIG. 1 and Table 2. In Table 2, "-50" in the material number represents 50 μg of the corresponding dsRNA per g of feed, i.e., "50 μg/g feed" as previously stated; "-5" represents 5 μg of the corresponding dsRNA per gram of feed, i.e., "5 μg/g feed" as previously stated. For example, "r1-dsRNA-50" represents 50 μg r1-dsRNA per gram of feed. "DAI" represents the number of days after incubating and feeding the insects.

The measured results of expression amount of the target gene in FIG. 1 showed that dsRNA (50 μg/g feed) of the target sequence c46312_g1-01 had significant inhibition effect on the expression of the target gene c46312 in the *Monolepta hieroglyphica* (Motschulsky), and the expression amount of the target gene c46312 was significantly down-regulated on day 4 of feeding, the expression of the target gene c46312 were almost not detected on day 10.

The results of feeding with dsRNA in Table 2 showed that the dsRNA of target sequences c46312_g1-01 to c46312_g1-04 of the target gene c46312 had significant lethal effect on the *Monolepta hieroglyphica* (Motschulsky), and there were no surviving larvae in most repeats on day 14 of feeding.

protein is exposed from the ribosome, signal recognition particle 54 kDa protein rapidly binds to the signal sequence of the pre-secreted protein and transfers it to the translocation chain related membrane protein. The related literature showed that interfering with coding gene expression of signal recognition particle 54 kDa protein can have lethal effects on a variety of *Coleoptera* insects, as reported by Julia Ulrich et al. (2015), RNAi interference was performed on the coding gene of the protein in the Tribolium castaneum by an injection manner (injection sequence code of iB_00404), and it was found that almost all Tribolium castaneum were killed at about four days after injection. As also reported by Avet-Rochex et al. (2010), RNAi interference was performed on the coding gene of the protein in *Drosophila* by an injection manner (Table 1), and the results showed that almost all *Drosophila* were killed after injection.

On the basis of the reports in the above-mentioned literatures and the high homology of the sequences, the coding gene of this protein in *Monolepta hieroglyphica* (Motschulsky) was screened out. As for sequences for injection into Tribolium castaneum and *Drosophila*, the sequence M1 at corresponding position was selected, as shown in SEQ ID NO: 16, and the sequence M2 at non-corresponding position was selected, as shown in SEQ ID NO: 17. The control ability for *Monolepta hieroglyphica* (Motschulsky) was determined by using a method of feeding dsRNA (at a ratio of 50 μg/g of feed) in the Example 3 of the present invention. As shown in Table 3, the experimental results showed that neither the sequence M1 at the corresponding position, nor the sequence M2 at the non-corresponding position can produce a significant lethal effect on *Monolepta hieroglyphica* (Motschulsky), which was basically no different from the control group. Similar experimental results were confirmed in PCT international public patent WO 2018/026770, which was verified with RNAi lethal genes of *Nematodes, Drosophila* and so on after transcriptome was obtained, that is, according to the known several lethal genes of *Nematodes* and *Drosophila*, RNAi

TABLE 2

Experimental results of survival rate of *Monolepta hieroglyphica* (Motschulsky) fed with dsRNA

| Material Number | DAI0 | DAI2 | DAI4 | DAI6 | DAI8 | DAI10 | DAI12 | DAI14 |
| --- | --- | --- | --- | --- | --- | --- | --- | --- |
| CK-dsRNA | 100% ± 0% | 100% ± 0% | 98% ± 3% | 95% ± 4% | 91% ± 8% | 88% ± 9% | 853% ± 11% | 83% ± 11% |
| c46312_g1-01-50 | 100% ± 0% | 100% ± 0% | 97% ± 3% | 93% ± 5% | 82% ± 3% | 65% ± 9% | 45% ± 11% | 30% ± 13% |
| c46312_g1-01-5 | 100% ± 0% | 100% ± 0% | 97% ± 4% | 92% ± 7% | 84% ± 10% | 71% ± 8% | 51% ± 14% | 33% ± 20% |
| c46312_g1-02-50 | 100% ± 0% | 100% ± 0% | 98% ± 3% | 93% ± 8% | 68% ± 24% | 48% ± 29% | 22% ± 20% | 12% ± 19% |
| c46312_g1-02-5 | 100% ± 0% | 100% ± 0% | 93% ± 4% | 92% ± 5% | 89% ± 11% | 74% ± 8% | 47% ± 12% | 42% ± 14% |
| c46312_g1-03-50 | 100% ± 0% | 100% ± 0% | 99% ± 2% | 96% ± 3% | 88% ± 6% | 50% ± 8% | 42% ± 12% | 21% ± 11% |
| c46312_g1-03-5 | 100% ± 0% | 100% ± 0% | 98% ± 1% | 93% ± 6% | 90% ± 8% | 73% ± 6% | 54% ± 12% | 29% ± 13% |
| c46312_g1-04-50 | 100% ± 0% | 100% ± 0% | 98% ± 3% | 97% ± 4% | 90% ± 7% | 66% ± 9% | 44% ± 10% | 18% ± 12% |
| c46312_g1-04-5 | 100% ± 0% | 100% ± 0% | 96% ± 5% | 91% ± 6% | 91% ± 12% | 65% ± 9% | 59% ± 13% | 26% ± 15% |

Example 4. Unexpected Technical Effect of Interfering with the Same Gene Expression in Different Insects Signal recognition particle 54 kDa protein, which belongs to one of the peptide chains in the signal recognition particle complex, and its main function is that when the pre-secreted interference was performed on the corresponding gene in maize rootworm, and there was basically no significant lethal effect. In summary, the technical effect of interfering with the same gene expression of different insects was unpredictable, and it is not inevitably associated with the technical effect of known interference and the homology of sequences.

TABLE 3

Experimental results of lethality rate of *Monolepta hieroglyphica* (Motschulsky) fed with dsRNA

| Material Number | DAI 4 | DAI 6 | DAI 8 | DAI 10 | DAI 12 | DAI 14 |
| --- | --- | --- | --- | --- | --- | --- |
| CK-dsRNA | 96% ± 6% | 85% ± 9% | 75% ± 16% | 71% ± 16% | 69% ± 13% | 69% ± 14% |
| M1-dsRNA-50 | 98% ± 3% | 92% ± 6% | 89% ± 7% | 83% ± 9% | 69% ± 15% | 63% ± 18% |
| M2-dsRNA-50 | 91% ± 8% | 88% ± 10% | 84% ± 11% | 76% ± 13% | 69% ± 15% | 67% ± 17% |

Example 5. Construction of Plant Expression Vectors

Figure 2:
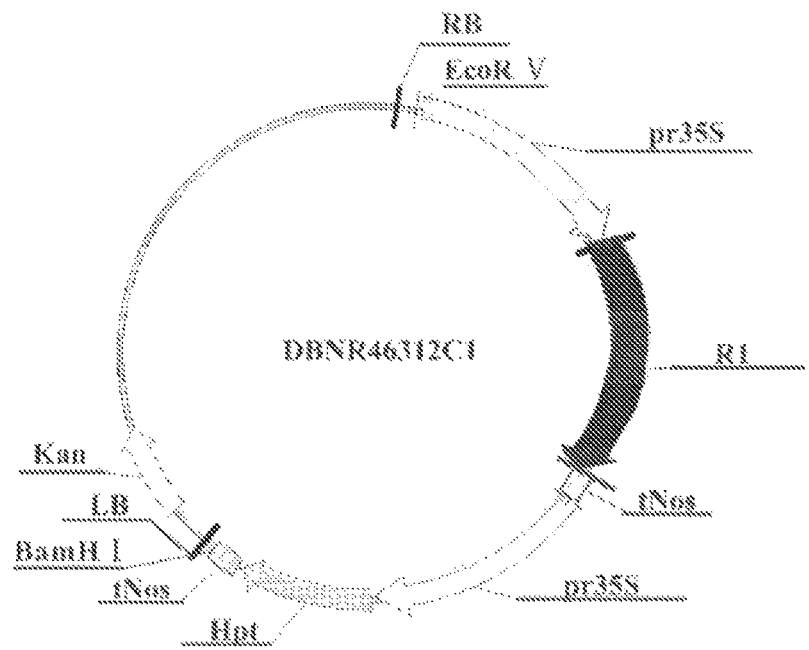
FIG. 2 is a schematic diagram of recombinant expression vector DBNR46312C1 used in the polynucleotide and method for controlling insect invasions according to the present invention.

Two expression cassettes were synthesized according to the order of p35S-RX-tNos-p35S-Hpt-tNos (X is 1-4), and connected to the plant expression vectors through EcoR V and BamH I, and named DBNR46312CX (X is 1-4, in which the vector schematic diagram of DBNR46312C1 was shown in FIG. 2 (Kan: Kanamycin gene; RB: the right boundary; pr35S: cauliflower mosaic virus 35S (SEQ ID NO: 7); R1 (SEQ ID NO: 8): the g1_01 nucleotide sequence (g1_01 is the target sequence 1 of target gene c46312, SEQ ID NO: 3)+spacer sequence (SEQ ID NO: 9)+the reverse complementary sequence of the r1 nucleotide sequence; tNos: the terminator of nopaline synthase gene (SEQ ID NO: 10); Hpt: hygromycin phosphotransferase gene (SEQ ID NO: 11); and LB: the left border).

*Escherichia coli* T1 competent cells were transformed with the recombinant expression vector DBNR46312C1 by a heat shock method with the following heat shock conditions: water bathing 50 μL of *Escherichia coli* T1 competent cells and 10 μL of plasmid DNA (recombinant expression vector DBNR46312C1) at 42° C. for 30 s; shake culturing at 37° C. for 1 h (using a shaker at a rotation speed of 100 rpm for shaking); then culturing under the condition of a temperature of 37° C. for 12 h on a LB solid plate (10 g/L of tryptone, 5 g/L of yeast extract, 10 g/L of NaCl, and 15 g/L of agar, adjusted to a pH of 7.5 with NaOH) containing 50 mg/L of Kanamycin, picking white colonies, and culturing under the conditions of a temperature of 37° C. overnight in a LB liquid culture medium (10 g/L of tryptone, 5 g/L of yeast extract, 10 g/L of NaCl, and 50 mg/L of Kanamycin, adjusted to a pH of 7.5 with NaOH). The plasmids in the cells were extracted through an alkaline method: centrifuging the bacteria solution at a rotation speed of 12000 rpm for 1 min, removing the supernatant, and the precipitated bacteria were suspended with 100 μL of an ice precooled solution I (25 mM of Tris-HCl, 10 mM of EDTA (ethylenediamine tetraacetic acid), 50 mM of glucose, pH 8.0); adding 200 μL of a freshly prepared solution II (0.2 M of NaOH, 1% SDS (sodium dodecyl sulfate)), reversing the tube 4 times, mixing, and placing on ice for 3-5 min; adding 150 μL of a cold solution III (3M of potassium acetate, 5M of acetic acid), mixing evenly well immediately, and placing on ice for 5-10 min; centrifuging under the conditions of a temperature of 4° C. and a rotation speed of 12000 rpm for 5 min, adding 2 times of volume of anhydrous ethanol to the supernatant, mixing evenly and placing at room temperature for 5 min; centrifuging under the conditions of a temperature of 4° C. and a rotation speed of 12000 rpm for 5 min, discarding the supernatant, and washing the precipitate with ethanol at a concentration (V/V) of 70% and drying; adding 30 μL of TE (10 mM of Tris-HCl, 1 mM of EDTA, pH 8.0) containing RNase (20 μg/mL) to dissolve the precipitate; water bathing at 37° C. for 30 min to digest RNA; storing at −20° C. for later use. The extracted plasmids were sequenced and identified through PCR, and the results demonstrated that the recombinant expression vector DBNR46312C1 was correctly constructed.

According to the above-mentioned method, recombinant expression vectors DBNR46312C2-DBNR46312C4 were constructed respectively, with the following vector structures: Kan: Kanamycin gene; RB: the right boundary; pr35S: cauliflower mosaic virus 35S (SEQ ID NO: 7); RX: the g1_0X nucleotide sequence (g1_0X is the target sequence X of target gene c46312, X is 2-4)+spacer sequence (SEQ ID NO: 9)+the reverse complementary sequence of the g1_0X nucleotide sequence); tNos: the terminator of nopaline synthase gene (SEQ ID NO: 10); Hpt: hygromycin phosphotransferase gene (SEQ ID NO: 11); and LB: the left boundary. *Escherichia coli* T1 competent cells were transformed respectively with the recombinant expression vector DBNR46312C2-DBNR46312C4 by a heat shock method, and the plasmids in the cells were extracted through an alkaline method.

Example 6. Transformation of *Agrobacterium* with the Recombinant Expression Vectors

*Agrobacterium* LBA4404 (Invitrogen, Chicago, USA, CAT: 18313-015) was transformed respectively with the recombinant expression vectors DBN46312C1-DBNR46312C4 which had been correctly constructed, by using a liquid nitrogen method with the following transformation conditions: placing 100 μL of *Agrobacterium* LBA4404, and 3 μL of plasmid DNA (recombinant expression vector) in liquid nitrogen for 10 min, and warm water bathing at 37° C. for 10 min; inoculating the transformed *Agrobacterium* LBA4404 into a LB tube, culturing under the conditions of a temperature of 28° C. and a rotation speed of 200 rpm for 2 h, and then spreading on a LB plate containing 50 mg/L of rifampicin and 100 mg/L of Kanamycin until positive single clones were grown, picking out single clones for culturing and extracting the plasmids thereof, and performing verification by enzyme digestion on the recombinant expression vectors DBNR46312C1-DBNR46312C4 with restriction endonucleases EcoR V and BamH I, with the results demonstrating that the structures of the recombinant expression vectors DBNR46312C1-DBNR46312C4 were completely correct.

Example 7. Acquisition of Transgenic Maize Plants

According to the conventionally used *Agrobacterium* infection method, young embryos of maize variety Zong31 (Z31) cultured under sterile conditions were co-cultured with the transformed *Agrobacterium* in Example 6, so as to transfer T-DNA (comprising the RX nucleotide sequence, a promoter sequence of a cauliflower mosaic virus 35S gene, a Hpt gene and a Nos terminator sequence) in the recombinant expression vectors DBNR46312C1-DBNR46312C4 constructed in Example 5 into the maize chromosome, thereby obtaining maize plants with the RX nucleotide sequence (X is 1-4) incorporated; meanwhile, wild type maize plants were used as the control.

As regards the *Agrobacterium*-mediated maize transformation, briefly, immature young embryos were separated from maize, and contacted with an *Agrobacterium* suspension, wherein the *Agrobacterium* can transfer the RX nucleotide sequence to at least one cell of one of the young embryos (step 1: the infection step). In this step, the young embryos were preferably immersed in an *Agrobacterium* suspension ($OD_{660}$=0.4-0.6, a culture medium for infection (4.3 g/L of MS salt, MS vitamin, 300 mg/L of casein, 68.5 g/L of sucrose, 36 g/L of glucose, 40 mg/L of acetosyringone (AS), and 1 mg/L of 2,4-dichlorophenoxyacetic acid (2,4-D), pH 5.3)) to initiate the inoculation. The young embryos were co-cultured with *Agrobacterium* for a period of time (3 days) (step 2: the co-culturing step). Preferably, the young embryos were cultured in a solid culture medium (4.3 g/L of MS salt, MS vitamin, 300 mg/L of casein, 20 g/L of sucrose, 10 g/L of glucose, 100 mg/L of acetosyringone (AS), 1 mg/L of 2,4-dichlorophenoxyacetic acid (2,4-D), and 8 g/L of agar, pH 5.8) after the infection step. After this co-culturing stage, there can be an optional "recovery" step. In the "recovery" step, there may be at least one antibiotic (cephalosporin) known to inhibit the growth of *Agrobacterium* in a culture medium for recovery (4.3 g/L of MS salt, MS vitamin, 300 mg/L of casein, 30 g/L of sucrose, 1 mg/L of 2,4-dichlorophenoxyacetic acid (2,4-D), and 3 g/L of phytagel, pH 5.8), without the addition of a selective agent for plant transformant (step 3: the recovery step). Preferably, the young embryos were cultured in a solid culture medium with the antibiotic, but without the selective agent, to eliminate *Agrobacterium* and provide a recovery stage for the infected cells. Subsequently, the inoculated young embryos were cultured in a culture medium containing a selective agent (hygromycin), and growing transformed calli were selected (step 4: the selection step). Preferably, the young embryos were cultured in a solid culture medium for screening (4.3 g/L of MS salt, MS vitamin, 300 mg/L of casein, 30 g/L of sucrose, 50 mg/L of hygromycin, 1 mg/L of 2,4-dichlorophenoxyacetic acid (2,4-D), and 3 g/L of phytagel, pH 5.8) with the selective agent, resulting in selective growth of transformed cells. Then, plants were regenerated from the calli (step 5: the regeneration step). Preferably, the calli grown on a culture medium containing the selective agent were cultured in solid culture media (MS differentiation culture medium and MS rooting culture medium) to regenerate plants.

The resistant calli obtained from screening were transferred onto the MS differentiation culture medium (4.3 g/L of MS salt, MS vitamin, 300 mg/L of casein, 30 g/L of sucrose, 2 mg/L of 6-benzyladenine, 50 mg/L of hygromycin, and 3 g/L of phytagel, pH 5.8), and cultured at 25° C. for differentiation. The differentiated seedlings were transferred onto the MS rooting culture medium (2.15 g/L of MS salt, MS vitamin, 300 mg/L of casein, 30 g/L of sucrose, 1 mg/L of indole-3-acetic acid, and 3 g/L of phytagel, pH 5.8), cultured at 25° C. until reaching a height of about 10 cm, and transferred to a greenhouse for culturing until fruiting. In the greenhouse, the plants were cultured at 28° C. for 16 hours, and then cultured at 20° C. for 8 hours every day.

Example 8. Acquisition of Transgenic Soybean Plants

According to the conventionally used *Agrobacterium* infection method, cotyledonary node tissues of soybean variety Zhonghuang13 cultured under sterile conditions were co-cultured with the transformed *Agrobacterium* in Example 6, so as to transfer T-DNA (comprising the RX nucleotide sequence, a promoter sequence of a cauliflower mosaic virus 35S gene, a Hpt gene and a Nos terminator sequence) in the recombinant expression vectors DBNR46312C1-DBNR46312C4 constructed in Example 5 into the soybean chromosome, thereby obtaining soybean plants with the RX nucleotide sequence (X is 1-4) incorporated; meanwhile, wild type soybean plants were used as the control.

As regards the *Agrobacterium*-mediated soybean transformation, briefly, mature soybean seeds were germinated in a culture medium for soybean germination (3.1 g/L of B5 salt, B5 vitamin, 20 g/L of sucrose, and 8 g/L of agar, pH 5.6), and the seeds were inoculated on the culture medium for germination and cultured under the conditions of a temperature of 25±1° C.; and a photoperiod (light/dark) of 16h/8h. After 4-6 days of germination, soybean sterile seedlings swelling at bright green cotyledonary nodes were taken, hypocotyls were cut off 3-4 mm below the cotyledonary nodes, the cotyledons were cut longitudinally, and apical buds, lateral buds and seminal roots were removed. A wound was made at a cotyledonary node using the knife back of a scalpel, the wounded cotyledonary node tissues were contacted with an *Agrobacterium* suspension, wherein the *Agrobacterium* can transfer the RX nucleotide sequence to the wounded cotyledonary node tissues (step 1: the infection step). In this step, the cotyledonary node tissues were preferably immersed in the *Agrobacterium* suspension ($OD_{660}$=0.5-0.8, a culture medium for infection (2.15 g/L of MS salt, B5 vitamin, 20 g/L of sucrose, 10 g/L of glucose, 40 mg/L of acetosyringone (AS), 4 g/L of 2-morpholine ethanesulfonic acid (MES), and 2 mg/L of zeatin (ZT), pH 5.3)) to initiate the inoculation. The cotyledonary node tissues were co-cultured with the *Agrobacterium* for a period of time (3 days) (step 2: the co-culturing step). Preferably, the cotyledonary node tissues were cultured in a solid culture medium (4.3 g/L of MS salt, B5 vitamin, 20 g/L of sucrose, 10 g/L of glucose, 4 g/L of 2-morpholine ethanesulfonic acid (MES), 2 mg/L of zeatin, and 8 g/L of agar, pH 5.6) after the infection step. After this co-culturing stage, there can be an optional "recovery" step. In the "recovery" step, there may be at least one antibiotic (cephalosporin) known to inhibit the growth of *Agrobacterium* in a culture medium for recovery (3.1 g/L of B5 salt, B5 vitamin, 1 g/L of 2-morpholine ethanesulfonic acid (MES), 30 g/L of sucrose, 2 mg/L of zeatin (ZT), 8 g/L of agar, 150 mg/L of cephalosporin, 100 mg/L of glutamic acid, and 100 mg/L of aspartic acid, pH 5.6), without the addition of a selective agent for plant transformant (step 3: the recovery step).

Preferably, tissue blocks regenerated from the cotyledonary nodes were cultured in a solid culture medium with the antibiotic, but without the selective agent, to eliminate *Agrobacterium* and provide a recovery stage for the infected cells. Subsequently, the tissue blocks regenerated from the cotyledonary nodes were cultured in a culture medium containing a selective agent (hygromycin), and growing transformed calli were selected (step 4: the selection step). Preferably, the tissue blocks regenerated from the cotyledonary nodes were cultured in a solid culture medium for screening (3.1 g/L of B5 salt, B5 vitamin, 1 g/L of 2-morpholine ethanesulfonic acid (MES), 30 g/L of sucrose, 1 mg/L of 6-benzyladenine (6-BAP), 8 g/L of agar, 150 mg/L of cephalosporin, 100 mg/L of glutamic acid, 100 mg/L of aspartic acid, and 50 mg/L of hygromycin, pH 5.6) with the selective agent, resulting in selective growth of transformed cells. Then, plants were regenerated from the transformed cells (step 5: the regeneration step). Preferably, the tissue blocks regenerated from the cotyledonary nodes grown on a culture medium containing the selective agent were cultured in solid culture media (B5 differentiation culture medium and B5 rooting culture medium) to regenerate plants.

The resistant tissue blocks obtained from screening were transferred onto the B5 differentiation culture medium (3.1 g/L of B5 salt, B5 vitamin, 1 g/L of 2-morpholine ethanesulfonic acid (MES), 30 g/L of sucrose, 1 mg/L of zeatin (ZT), 8 g/L of agar, 150 mg/L of cephalosporin, 50 mg/L of glutamic acid, 50 mg/L of aspartic acid, 1 mg/L of gibberellin, 1 mg/L of auxin, and 50 mg/L of hygromycin, pH 5.6), and cultured at 25° C. for differentiation. The differentiated seedlings were transferred onto the B5 rooting culture medium (3.1 g/L of B5 salt, B5 vitamin, 1 g/L of 2-morpholine ethanesulfonic acid (MES), 30 g/L of sucrose, 8 g/L of agar, 150 mg/L of cephalosporin, and 1 mg/L of indole-3-butyric acid (IBA)), cultured on the rooting culture medium at 25° C. until reaching a height of about 10 cm, and transferred to a greenhouse for culturing until fruiting. In the greenhouse, the plants were cultured at 26° C. for 16 hours, and then cultured at 20° C. for 8 hours every day.

Example 9. Verification of the Transgenic Maize Plants and the Transgenic Soybean Plants Using TaqMan About 100 mg of leaves from the maize plants into which the RX nucleotide sequence (X is 1-4) was incorporated, were taken as samples. The genomic DNA thereof was extracted with a DNeasy Plant Maxi Kit from Qiagen respectively, and the copy number of a Hpt gene was detected by the Taqman probe fluorescence quantitative PCR method so as to determine the copy numbers of the RX nucleotide sequence. Meanwhile, wild type maize plants were used as the control, and detected and analyzed according to the above-mentioned method. Triple repeats were set for the experiments, and were averaged.

The particular method for detecting the copy number of the Hpt gene was as follows:

Step 901. 100 mg of leaves from the maize plants into which the RX nucleotide sequence was incorporated and wild type maize plants were respectively taken, ground into a homogenate in a mortar with liquid nitrogen, and triple repeats were taken for each sample;

Step 902. The genomic DNA of the above-mentioned samples was extracted using a DNeasy Plant Mini Kit from Qiagen, and the particular method can refer to the product instruction thereof;

Step 903. The concentrations of the genomic DNAs of the above-mentioned samples were detected using Nano-Drop 2000 (Thermo Scientific);

Step 904. The concentrations of the genomic DNAs of the above-mentioned samples were adjusted to a consistent concentration value which ranges from 80-100 ng/μL;

Step 905. The copy numbers of the samples were identified using the Taqman probe fluorescence quantitative PCR method, wherein samples for which the copy numbers had been identified and known were taken as standards, the samples of the wild type maize plants were taken as the control, and triple repeats were taken for each sample, and were averaged; the sequences of the primers and probe for fluorescence quantitative PCR were as follows, respectively:

The following primers and probe were used for detecting the Hpt nucleotide sequence:

Primer 1: cagggtgtcacgttgcaaga as shown in SEQ ID NO: 12 of the sequence listing;

Primer 2: ccgctcgtctggctaagatc as shown in SEQ ID NO: 13 of the sequence listing;

Probe 1: tgcctgaaaccgaactgcccgctg as shown in SEQ ID NO: 14 of the sequence listing;

| PCR Reaction System: | |
| --- | --- |
| JumpStart ™ Taq ReadyMix ™ (Sigma) | 10 μL |
| 50× primer/probe mixture | 1 μL |
| genomic DNA | 3 μL |
| water (ddH$_2$O) | 6 μL |

The 50×primer/probe mixture comprises 45 μL of each primer at a concentration of 1 mM, 50 μL of the probe at a concentration of 100 μM, and 860 μL of 1×TE buffer, and was stored at 4° C. in an centrifuge tube.

| PCR Reaction Conditions: | | |
| --- | --- | --- |
| Step | Temperature | Time |
| 911 | 95° C. | 5 min |
| 912 | 95° C. | 30 s |
| 913 | 60° C. | 1 min |
| 914 | back to step 912, repeated 40 times | |

Data was analyzed using software SDS2. 3 (Applied Biosystems).

By analyzing the experimental results of the copy number of the Hpt gene, it was further demonstrated whether the RX nucleotide sequence was respectively incorporated into the chromosome of the detected maize plants, and whether the maize plants into which the RX nucleotide sequence (X is 1-4) was incorporated resulted in single-copy transgenic maize plants.

According to the above-mentioned method of verifying the transgenic maize plants using TaqMan, the transgenic soybean plants were detected and analyzed. It was further demonstrated, by analyzing the experimental results of the copy number of the Hpt gene, that the RX nucleotide sequence was incorporated into the chromosomes of the detected soybean plants, and the soybean plants into which the RX nucleotide sequence (X is 1-4) was incorporated resulted in single-copy transgenic soybean plants.

Example 10. Identification of Insecticidal Effect of Transgenic Maize on *Monolepta hieroglyphica* (Motschulsky)

The insecticidal effect against *Monolepta hieroglyphica* (Motschulsky) of the maize plants into which the RX nucleotide sequence (X is 1-4) was incorporated was detected.

Step 1001. Ten strains of DBNR46312C1-DBNR46312C4 maize transformation events (RX-M), each of which was identified as a positive single copy through taqman, and three strains of maize transformation events (NGM1) which were identified as negative through taqman were chosen; meanwhile, wild type maize plants were used as the control (CK1); and the plants were grown in a greenhouse until trefoil stage;

Step 1002. The materials in step 1001 were taken, and a third young leaf was taken from each seedling, and cut to a size of 1×2 cm of leaf in which the main vein was removed, and laid and placed in a culture dish with a moist filter paper laid thereon;

Step 1003. 10 newly-incubated larvae of *Monolepta hieroglyphica* (Motschulsky) with an incubation time of not more than 24 h were placed in each dish, the covers of the dishes covered same tightly, the culture dishes were placed in a bioassay box with a moist piece of gauze laid at the bottom thereof, and the bioassay box was placed in a bioassay chamber at a temperature of 24±2° C., D/L of 24/0, and a humidity of 70%-80%;

Step 1004. Considering that the newly-incubated larvae of *Monolepta hieroglyphica* (Motschulsky) are small and weak, and easily suffer from mechanical injuries, it was better to keep the culture dishes unmoved on the day that the insects were incubated and 1 day after incubation;

Step 1005. Starting on day 2 after the incubation of the insects, the number of surviving *Monolepta hieroglyphica* (Motschulsky) was counted from the exterior of the culture dishes every day until the end of day 16; insects of *Monolepta hieroglyphica* (Motschulsky) surviving in the culture dishes were transferred to culture dishes charged with fresh leaves every two days, and the experimental results were shown in Table 4.

TABLE 4

Experimental results of feeding *Monolepta hieroglyphica* (Motschulsky) with leaves having maize transformation events

| Material number | Survival rate of *Monolepta hieroglyphica* (Motschulsky) at each two days after bioassay | | | | | | | |
|---|---|---|---|---|---|---|---|---|
| | DAI2 | DAI4 | DAI6 | DAI8 | DAI10 | DAI12 | DAI14 | DAI16 |
| CK1 | 100% ± 0% | 98% ± 4% | 92% ± 4% | 85% ± 8% | 82% ± 9% | 80% ± 8% | 76% ± 9% | 71% ± 8% |
| NGM1 | 100% ± 0% | 100% ± 0% | 95% ± 2% | 93% ± 5% | 87% ± 7% | 84% ± 10% | 80% ± 8% | 75% ± 10% |
| R1-M | 100% ± 0% | 100% ± 0% | 91% ± 1% | 92% ± 6% | 81% ± 10% | 67% ± 15% | 57% ± 12% | 37% ± 10% |
| R2-M | 100% ± 0% | 100% ± 0% | 94% ± 4% | 91% ± 6% | 82% ± 9% | 69% ± 14% | 58% ± 8% | 36% ± 9% |
| R3-M | 100% ± 0% | 100% ± 0% | 91% ± 4% | 91% ± 6% | 82% ± 10% | 69% ± 12% | 51% ± 13% | 35% ± 15% |
| R4-M | 100% ± 0% | 100% ± 0% | 99% ± 5% | 93% ± 6% | 82% ± 9% | 61% ± 7% | 60% ± 9% | 50% ± 13% |

The experimental results in Table 4 demonstrated that the maize plants into which the RX nucleotide sequence (X is 1-4) was incorporated had good inhibitory effects on *Monolepta hieroglyphica* (Motschulsky), and the survival rate (survival rate = survival number/test number) of *Monolepta hieroglyphica* (Motschulsky) was about 40% on day 16.

Example 11. Identification of Insecticidal Effect of Transgenic Soybean on *Monolepta hieroglyphica* (Motschulsky)

The insecticidal effect against *Monolepta hieroglyphica* of the soybean plants into which the RX nucleotide sequence (X is 1-4) was incorporated was detected.

Step 1101. Ten strains of DBNR46312C1-DBNR46312C4 soybean transformation events (RX-S) each of which was identified as a positive single copy through taqman, and three strains of soybean transformation events (NGM2) which were identified as negative through taqman were chosen; meanwhile, wild type soybean plants were used as the control (CK2); and the plants were grown in a greenhouse until three pieces of euphylla were grown;

Step 1102. The materials in step 1101 were taken, and a piece of euphylla with a size of about 2×2 cm was taken from each seedling, and laid and placed in a culture dish with a moist filter paper laid thereon;

Step 1103. 15 newly-incubated larvae of *Monolepta hieroglyphica* (Motschulsky) with an incubation time of not more than 24 h were placed in each dish, the covers of the dishes covered same tightly, the culture dishes were placed in a bioassay box with a moist piece of gauze laid at the bottom thereof, and the bioassay box was placed in a bioassay chamber at a temperature of 24±2, D/L of 24/0, and a humidity of 70%-80%;

Step 1104. Considering that the newly-incubated larvae of *Monolepta hieroglyphica* (Motschulsky) are small and weak, and easily suffer from mechanical injuries, it was better to keep the culture dishes unmoved on the day that the insects were incubated and 1 day after incubation;

Step 1105. Starting on day 2 after the incubation of the insects, the number of surviving *Monolepta hieroglyphica* (Motschulsky) was counted from the exterior of the culture dishes every day until the end of day 16; insects of *Monolepta hieroglyphica* (Motschulsky) surviving in the culture dishes were transferred to culture dishes charged with fresh euphylla every two days, and the experimental results were shown in Table 5.

TABLE 5

Experimental results of feeding *Monolepta hieroglyphica* (Motschulsky) with euphylla having soybean transformation events

| Material number | Survival rate of *Monolepta hieroglyphica* (Motschulsky) at each two days after bioassay | | | | | | | |
|---|---|---|---|---|---|---|---|---|
| | DAI2 | DAI4 | DAI6 | DAI8 | DAI10 | DAI12 | DAI14 | DAI16 |
| CK2 | 100% ± 0% | 100% ± 0% | 95% ± 3% | 94% ± 4% | 90% ± 4% | 86% ± 8% | 80% ± 9% | 74% ± 8% |
| NGM2 | 100% ± 0% | 100% ± 0% | 95% ± 2% | 93% ± 5% | 87% ± 7% | 84% ± 10% | 80% ± 8% | 75% ± 10% |
| R1-S | 100% ± 0% | 93% ± 5% | 93% ± 7% | 81% ± 10% | 62% ± 14% | 52% ± 10% | 40% ± 13% | 39% ± 13% |
| R2-S | 100% ± 0% | 94% ± 4% | 94% ± 7% | 84% ± 11% | 68% ± 11% | 57% ± 11% | 36% ± 10% | 44% ± 10% |
| R3-S | 100% ± 0% | 98% ± 2% | 93% ± 6% | 83% ± 10% | 53% ± 6% | 58% ± 12% | 38% ± 14% | 42% ± 14% |
| R4-S | 100% ± 0% | 93% ± 1% | 95% ± 7% | 82% ± 11% | 68% ± 12% | 52% ± 12% | 45% ± 9% | 42% ± 9% |

The experimental results in Table 5 demonstrated that the soybean plants into which the RX nucleotide sequence (X is 1-4) was incorporated had good inhibitory effects on *Monolepta hieroglyphica* (Motschulsky), and the survival rate (survival rate = survival number/test number) of *Monolepta hieroglyphica* (Motschulsky) was up to 50% on day 16.

Example 12. Composition

Formula of an agriculturally acceptable vector carrier for dsRNA (1 L system): 50 mM of $NaHPO_4$ (pH7.0), 10 mM of β-mercaptoethanol, 10 mM of EDTA, sodium hexadecylsulfonate at a mass fraction of 0.1%, and polyethylene glycol octyl phenyl ether at a mass fraction of 0.1%, make up to 1 L with $H_2O$.

The above-mentioned formula was a buffer formula, provided that any purified dsRNA is directly added to the buffer so that the final concentration met requirements, such as 50 mg/L. The formula can also be prepared into a concentrated preparation as desired.

In summary, the present invention discloses, for the first time, a target gene c46312 and target sequence thereof for controlling an insect pest of *Coleoptera, Monolepta hieroglyphica* (Motschulsky), and transgenic plants (maize and soybean) obtained by using RNAi technology. The transgenic plants control the invasion of *Monolepta hieroglyphica* (Motschulsky) efficiently and specifically by introducing dsRNA sequences formed from the target sequences, and *Monolepta hieroglyphica* (Motschulsky) can be prevented from developing an analogous risk of Bt-toxin protein resistance, with the advantages of good environment compatibility, convenience and low cost.

Finally, it should be stated that the above examples are merely used for illustrating, rather than limiting, the technical solution of the present invention; and although the present invention has been illustrated in detail with reference to the preferred examples, a person skilled in the art should understand that modifications or equivalent replacements may be made to the technical solution of the present invention without departing from the spirit and scope of the technical solution of the present invention.

What is claimed is:

1. An isolated polynucleotide for controlling a coleopteran insect pest comprising a heterologous promoter operably linked to a polynucleotide, wherein the polynucleotide comprises a polynucleotide sequence that is at least 99% identical to a fragment of SEQ ID NO:1 that is at least 123 nucleotides in length and a sequence complementary to the polynucleotide sequence, wherein when the coleopteran insect pest ingests a double-stranded RNA encoded by said polynucleotide sequence, the growth of the coleopteran insect pest is inhibited, and wherein the coleopteran insect pest is *Monolepta hieroglyphica*.

2. The polynucleotide according to claim 1, wherein the polynucleotide also comprises a spacer sequence.

3. The polynucleotide according to claim 2, wherein the spacer sequence is SEQ ID NO: 9.

4. An expression cassette or a recombinant vector comprising the polynucleotide according to claim 1.

5. An interfering ribonucleic acid encoded by the polynucleotide according to claim 1.

6. The interfering ribonucleic acid according to claim 5, wherein the interfering ribonucleic acid comprises at least two silencing elements, each of which comprises a nucleotide sequence at least partially complementary to a target sequence within the target gene.

7. The interfering ribonucleic acid according to claim 6, wherein each of the silencing elements comprises a different nucleotide sequence complementary to a different target sequence.

8. The interfering ribonucleic acid according to claim 7, wherein the different target sequence is derived from a single target gene or from a target gene different from the target gene.

9. The interfering ribonucleic acid according to claim 8, wherein the target gene different from the target gene is derived from a same insect pest of *Monolepta hieroglyphica* or a different insect pest of *Coleoptera*.

10. The interfering ribonucleic acid according to claim 5, wherein the interfering ribonucleic acid also comprises a spacer sequence.

11. The interfering ribonucleic acid according to claim 10, wherein the spacer sequence is SEQ ID NO: 9.

12. A composition for controlling invasion of an insect pest of *Monolepta hieroglyphica*, comprising at least one of the interfering ribonucleic acids according to claim 5 or a host cell expressing or capable of expressing the interfering ribonucleic acid sequence, and at least one suitable carrier, excipient or diluent.

13. The composition according to claim 12, wherein the host cell is a bacterial cell.

14. The composition according to claim 12, wherein the composition is a solid, a liquid or a gel.

15. The composition according to claim 14, wherein the composition is an insecticidal spray.

16. The composition according to claim 12, wherein the composition also comprises at least one pesticide, wherein the pesticide is a chemical pesticide, a potato tuber-specific protein, a *Bacillus thuringiensis* insecticidal protein, a *Xenorhabdus ehlersii* insecticidal protein, a *Photorhabdus* insecticidal protein, a *Bacillus laterosporus* insecticidal protein or a *Bacillus sphaericus* insecticidal protein.

17. A method for producing a plant capable of controlling an insect pest of *Monolepta hieroglyphica*, comprising introducing one of the following into the plant:
the polynucleotide according to claim 1;
the expression cassette comprising the polynucleotide according to claim 1; or
the recombinant vector comprising the polynucleotide according to claim 1.

18. A method for controlling invasion of an insect pest of *Monolepta hieroglyphica* or protecting a plant from damage caused by an insect pest of *Monolepta hieroglyphica*, comprising introducing one of the following into the plant:
the polynucleotide according to claim 1;
the expression cassette comprising the polynucleotide according to claim 1.

* * * * *

UNITED STATES PATENT AND TRADEMARK OFFICE
CERTIFICATE OF CORRECTION

PATENT NO. : 12,037,584 B2
APPLICATION NO. : 16/972896
DATED : July 16, 2024
INVENTOR(S) : Aihong Zhang et al.

It is certified that error appears in the above-identified patent and that said Letters Patent is hereby corrected as shown below:

In the Claims

Column 44, Line 51, cancel the text beginning with "18. A method" to and ending "claim 1." in Line 57, and insert the following claim:
--18. A method for controlling invasion of an insect pest of *Monolepta hieroglyphica* or protecting a plant from damage caused by an insect pest of *Monolepta hieroglyphica*, comprising introducing one of the following into the plant:
    the polynucleotide according to claim 1;
    the expression cassette comprising the polynucleotide according to claim 1; or
    the recombinant vector comprising the polynucleotide according to claim 1.--

Signed and Sealed this
Twenty-ninth Day of October, 2024

Katherine Kelly Vidal
*Director of the United States Patent and Trademark Office*

SEQUENCE LISTING

```
<160> NUMBER OF SEQ ID NOS: 17

<210> SEQ ID NO 1
<211> LENGTH: 1009
<212> TYPE: DNA
<213> ORGANISM: Monolepta hieroglyphica

<400> SEQUENCE: 1
atgtcgtcaa acatacaaaa agcccagcaa ctaatggctg aggcagaaaa gaaggtttct      60
tcaagaggat tctttggctc tttgtttggt ggctcaagtc gaattgaaga tgctgtagaa     120
tgttaccaaa gggctgcaaa cctcttcaaa atggccaaga gttgggatgc tgcaggaaag     180
gcattctgtg aagcagccaa cctgcatgct agaagtggtg ctcgtcatga tgctgccaca     240
aactatgttg atgcagcaaa ttgttataaa aaggctgata taagtgaggc tgtaaactgt     300
ttgataaaag ccatagacat ttacactgag atgggtcgct tcactatggc tgcaaaacat     360
caccaaacta ttgcagaaat gtatgagact gatgctgtcg acctagagag agctgtgcaa     420
cactatgagc aagctgctga ctacttcaga ggggaggaaa gcaattcctc cgctaataaa     480
tgccttctga aagtggccca atatgcagcc caacttgaaa attatgaaaa agcaatacag     540
atctaccaag aagtggctta ttccgccctc gaaagctccc tcttgaagta cagtgctaaa     600
gaatatttgt ttagagctgc cctttgtcac ctttgtgttg atgtactcaa tgcccaacat     660
gccatagaaa gttatatcca aaggtatccg gcatttcaag attctcgtga atataaactt     720
ttgaaaacgc ttatagaaca cattgaggaa caaaatgtcg atggctacac agatgcagtg     780
```

```
aaagactatg attccatttc tcgcctggat caatggtata caacaattct tttacgtatt      840
aaaaaacaac tcaacgagag ccccgacttg cgctaaattg tatttattgg aattccttat      900
tgttcatatt tgttacgtgt tataataaaa gacccatagt ttatttattg ttgaattatt      960
agttaaattt tttatgtctt atgcataaaa gttatttggt ctggagata                 1009
```

<210> SEQ ID NO 2
<211> LENGTH: 291
<212> TYPE: PRT
<213> ORGANISM: Monolepta hieroglyphica

<400> SEQUENCE: 2

```
Met Ser Ser Asn Ile Gln Lys Ala Gln Gln Leu Met Ala Glu Ala Glu
1               5                   10                  15

Lys Lys Val Ser Ser Arg Gly Phe Phe Gly Ser Leu Phe Gly Gly Ser
            20                  25                  30

Ser Arg Ile Glu Asp Ala Val Glu Cys Tyr Gln Arg Ala Ala Asn Leu
        35                  40                  45

Phe Lys Met Ala Lys Ser Trp Asp Ala Ala Gly Lys Ala Phe Cys Glu
    50                  55                  60

Ala Ala Asn Leu His Ala Arg Ser Gly Ala Arg His Asp Ala Ala Thr
65                  70                  75                  80

Asn Tyr Val Asp Ala Ala Asn Cys Tyr Lys Lys Ala Asp Ile Ser Glu
                85                  90                  95

Ala Val Asn Cys Leu Ile Lys Ala Ile Asp Ile Tyr Thr Glu Met Gly
            100                 105                 110

Arg Phe Thr Met Ala Ala Lys His His Gln Thr Ile Ala Glu Met Tyr
        115                 120                 125

Glu Thr Asp Ala Val Asp Leu Glu Arg Ala Val Gln His Tyr Glu Gln
    130                 135                 140

Ala Ala Asp Tyr Phe Arg Gly Glu Glu Ser Asn Ser Ser Ala Asn Lys
145                 150                 155                 160

Cys Leu Leu Lys Val Ala Gln Tyr Ala Ala Gln Leu Glu Asn Tyr Glu
                165                 170                 175

Lys Ala Ile Gln Ile Tyr Gln Glu Val Ala Tyr Ser Ala Leu Glu Ser
            180                 185                 190

Ser Leu Leu Lys Tyr Ser Ala Lys Glu Tyr Leu Phe Arg Ala Ala Leu
        195                 200                 205

Cys His Leu Cys Val Asp Val Leu Asn Ala Gln His Ala Ile Glu Ser
    210                 215                 220

Tyr Ile Gln Arg Tyr Pro Ala Phe Gln Asp Ser Arg Glu Tyr Lys Leu
225                 230                 235                 240

Leu Lys Thr Leu Ile Glu His Ile Glu Glu Gln Asn Val Asp Gly Tyr
                245                 250                 255

Thr Asp Ala Val Lys Asp Tyr Asp Ser Ile Ser Arg Leu Asp Gln Trp
            260                 265                 270

Tyr Thr Thr Ile Leu Leu Arg Ile Lys Lys Gln Leu Asn Glu Ser Pro
        275                 280                 285

Asp Leu Arg
    290
```

<210> SEQ ID NO 3
<211> LENGTH: 541
<212> TYPE: DNA
<213> ORGANISM: Monolepta hieroglyphica

<400> SEQUENCE: 3

```
gatgggtcgc ttcactatgg ctgcaaaaca tcaccaaact attgcagaaa tgtatgagac    60
tgatgctgtc gacctagaga gagctgtgca acactatgag caagctgctg actacttcag   120
aggggaggaa agcaattcct ccgctaataa atgccttctg aaagtgggcccc aatatgcagc   180
ccaacttgaa aattatgaaa aagcaataca gatctaccaa gaagtggctt attccgccct   240
cgaaagctcc ctcttgaagt acagtgctaa agaatatttg tttagagctg ccctttgtca   300
cctttgtgtt gatgtactca atgcccaaca tgccatagaa agttatatcc aaaggtatcc   360
ggcatttcaa gattctcgtg aatataaact tttgaaaacg cttatagaac acattgagga   420
acaaaatgtc gatggctaca cagatgcagt gaaagactat gattccattt ctcgcctgga   480
tcaatggtat acaacaattc ttttacgtat taaaaaacaa ctcaacgaga gccccgactt   540
g                                                                  541
```

<210> SEQ ID NO 4
<211> LENGTH: 308
<212> TYPE: DNA
<213> ORGANISM: Monolepta hieroglyphica

<400> SEQUENCE: 4

```
gcccagcaac taatggctga ggcagaaaag aaggtttctt caagaggatt ctttggctct    60
ttgtttggtg gctcaagtcg aattgaagat gctgtagaat gttaccaaag ggctgcaaac   120
ctcttcaaaa tggccaagag ttgggatgct gcaggaaagg cattctgtga agcagccaac   180
ctgcatgcta gaagtggtgc tcgtcatgat gctgccacaa actatgttga tgcagcaaat   240
tgttataaaa aggctgatat aagtgaggct gtaaactgtt tgataaaagc catagacatt   300
tacactga                                                           308
```

<210> SEQ ID NO 5
<211> LENGTH: 123
<212> TYPE: DNA
<213> ORGANISM: Monolepta hieroglyphica

<400> SEQUENCE: 5

```
catgatgctg ccacaaacta tgttgatgca gcaaattgtt ataaaaaggc tgatataagt    60
gaggctgtaa actgtttgat aaaagccata gacatttaca ctgagatggg tcgcttcact   120
atg                                                                123
```

<210> SEQ ID NO 6
<211> LENGTH: 373
<212> TYPE: DNA
<213> ORGANISM: Monolepta hieroglyphica

<400> SEQUENCE: 6

```
ctattgcaga aatgtatgag actgatgctg tcgacctaga gagagctgtg caacactatg    60
agcaagctgc tgactacttc agaggggagg aaagcaattc ctccgctaat aaatgccttc   120
tgaaagtggc ccaatatgca gcccaacttg aaaattatga aaagcaata cagatctacc    180
aagaagtggc ttattccgcc ctcgaaagct ccctcttgaa gtacagtgct aaagaatatt   240
tgtttagagc tgccctttgt cacctttgtg ttgatgtact caatgcccaa catgccatag   300
aaagttatat ccaaaggtat ccggcatttc aagattctcg tgaatataaa cttttgaaaa   360
cgcttataga aca                                                     373
```

```
<210> SEQ ID NO 7
<211> LENGTH: 328
<212> TYPE: DNA
<213> ORGANISM: Cauliflower mosaic virus

<400> SEQUENCE: 7
ccattgccca gctatctgtc actttattgt gaagatagtg aaaaggaag gtggctccta      60 caaatgccat cattgcgata aaggaaaggc catcgttgaa gatgcctctg ccgacagtgg    120
tcccaaagat ggaccccac ccacgaggag catcgtggaa aaagaagacg ttccaaccac     180
gtcttcaaag caagtggatt gatgtgatat ctccactgac gtaagggatg acgcacaatc    240
ccactatcct tcgcaagacc cttcctctat ataaggaagt tcatttcatt tggagaggac    300
acgctgacaa gctgactcta gcagatct                                       328

<210> SEQ ID NO 8
<211> LENGTH: 1232
<212> TYPE: DNA
<213> ORGANISM: Artificial Sequence
<220> FEATURE:
<223> OTHER INFORMATION: R1 nucleotide sequence

<400> SEQUENCE: 8
gatgggtcgc ttcactatgg ctgcaaaaca tcaccaaact attgcagaaa tgtatgagac     60
tgatgctgtc gacctagaga gagctgtgca acactatgag caagctgctg actacttcag   120
aggggaggaa agcaattcct ccgctaataa atgccttctg aaagtggccc aatatgcagc   180
ccaacttgaa aattatgaaa aagcaataca gatctaccaa gaagtggctt attccgccct   240
cgaaagctcc ctcttgaagt acagtgctaa agaatatttg tttagagctg cccttttgtca  300 cctttgtgtt gatgtactca atgcccaaca tgccatagaa agttatatcc aaaggtatcc    360
ggcatttcaa gattctcgtg aatataaact tttgaaaacg cttatagaac acattgagga   420
acaaaatgtc gatggctaca cagatgcagt gaaagactat gattccattt ctcgcctgga   480
tcaatggtat acaacaattc ttttacgtat taaaaaacaa ctcaacgaga gccccgactt   540
gaagtactgc gatcgcgtta acgctttatc acgatacctt ctaccacata tcactaacaa   600
catcaacact catcactctc gacgacatcc actcgatcac tactctcaca cgaccgatta   660
actcctcatc cacgcggccg cctgcaggag ccaagtcggg gctctcgttg agttgttttt   720
taatacgtaa agaattgtt gtataccatt gatccaggcg agaaatggaa tcatagtctt    780
tcactgcatc tgtgtagcca tcgacatttt gttcctcaat gtgttctata gcgttttca    840 aaagtttata ttcacgagaa tcttgaaatg ccggatacct ttggatataa ctttctatgg   900
catgttgggc attgagtaca tcaacacaaa ggtgacaaag gcagctcta aacaaatatt     960 ctttagcact gtacttcaag agggagcttt cgagggcgga ataagccact tcttggtaga  1020
tctgtattgc tttttcataa ttttcaagtt gggctgcata ttgggccact tcagaaggc   1080 atttattagc ggaggaattg cttttcctccc ctctgaagta gtcagcagct tgctcatagt  1140
gttgcacagc tctctctagg tcgacagcat cagtctcata catttctgca atagtttggt  1200
gatgttttgc agccatagtg aagcgaccca tc                                 1232

<210> SEQ ID NO 9
<211> LENGTH: 150
<212> TYPE: DNA
<213> ORGANISM: Artificial Sequence
<220> FEATURE:
<223> OTHER INFORMATION: spacer sequence
```

<400> SEQUENCE: 9

```
aagtactgcg atcgcgttaa cgctttatca cgatacctte taccacatat cactaacaac     60
atcaacactc atcactctcg acgacatcca ctcgatcact actctcacac gaccgattaa    120
ctcctcatcc acgcggccgc ctgcaggagc                                     150
```

<210> SEQ ID NO 10
<211> LENGTH: 253
<212> TYPE: DNA
<213> ORGANISM: Agrobacterium tumefaciens

<400> SEQUENCE: 10

```
gatcgttcaa acatttggca ataaagtttc ttaagattga atcctgttgc cggtcttgcg     60
atgattatca tataatttct gttgaattac gttaagcatg taataattaa catgtaatgc    120
atgacgttat ttatgagatg ggttttatg attagagtcc cgcaattata catttaatac    180
gcgatagaaa acaaaatata gcgcgcaaac taggataaat tatcgcgcgc ggtgtcatct    240
atgttactag atc                                                       253
```

<210> SEQ ID NO 11
<211> LENGTH: 1026
<212> TYPE: DNA
<213> ORGANISM: Salmonella enterica

<400> SEQUENCE: 11

```
atgaaaaagc ctgaactcac cgcgacgtct gtcgagaagt ttctgatcga aaagttcgac     60
agcgtctccg acctgatgca gctctcggag ggcgaagaat ctcgtgcttt cagcttcgat    120
gtaggagggc gtggatatgt cctgcgggta aatagctgcg ccgatggttt ctacaaagat    180
cgttatgttt atcggcactt tgcatcggcc gcgctcccga ttccggaagt gcttgacatt    240
ggggaattca gcgagagcct gacctattgc atctcccgcc gtgcacaggg tgtcacgttg    300
caagacctgc ctgaaaccga actgcccgct gttctgcagc cggtcgcgga ggccatggat    360
gcgatcgctg cggccgatct tagccagacg agcgggttcg gcccattcgg accgcaagga    420
atcggtcaat acactacatg gcgtgatttc atatgcgcga ttgctgatcc ccatgtgtat    480
cactggcaaa ctgtgatgga cgacaccgtc agtgcgtccg tcgcgcaggc tctcgatgag    540
ctgatgcttt gggccgagga ctgccccgaa gtccggcacc tcgtgcacgc ggatttcggc    600
tccaacaatg tcctgacgga caatggccgc ataacagcgg tcattgactg gagcgaggcg    660
atgttcgggg attcccaata cgaggtcgcc aacatcttct tctggaggcc gtggttggct    720
tgtatggagc agcagacgcg ctacttcgag cggaggcatc cggagcttgc aggatcgccg    780
cggctccggg cgtatatgct ccgcattggt cttgaccaac tctatcagag cttggttgac    840
ggcaatttcg atgatgcagc ttgggcgcag gtcgatgcg acgcaatcgt ccgatccgga    900
gccgggactg tcgggcgtac acaaatcgcc cgcagaagcg cggccgtctg gaccgatggc    960
tgtgtagaag tactcgccga tagtggaaac cgacgcccca gcactcgtcc gagggcaaag   1020
gaatag                                                              1026
```

<210> SEQ ID NO 12
<211> LENGTH: 20
<212> TYPE: DNA
<213> ORGANISM: Artificial Sequence
<220> FEATURE:
<223> OTHER INFORMATION: primer 1

<400> SEQUENCE: 12

```
cagggtgtca cgttgcaaga                                                      20

<210> SEQ ID NO 13
<211> LENGTH: 20
<212> TYPE: DNA
<213> ORGANISM: Artificial Sequence
<220> FEATURE:
<223> OTHER INFORMATION: primer 2

<400> SEQUENCE: 13
ccgctcgtct ggctaagatc                                                      20

<210> SEQ ID NO 14
<211> LENGTH: 24
<212> TYPE: DNA
<213> ORGANISM: Artificial Sequence
<220> FEATURE:
<223> OTHER INFORMATION: probe

<400> SEQUENCE: 14
tgcctgaaac cgaactgccc gctg                                                 24

<210> SEQ ID NO 15
<211> LENGTH: 334
<212> TYPE: DNA
<213> ORGANISM: Artificial Sequence
<220> FEATURE:
<223> OTHER INFORMATION: irrelevant dsRNA

<400> SEQUENCE: 15
ggaaatcgcc actgctaaga aaatggaca gaaaaataag agagcggcac ttcaagcact           60
caagcggaag aagcggtatg agaaacagtt gcagcagatt gatggaacat tatcaactat         120
tgaaatgcag agagaagctt tagagggtgc caacactaat acagctgttc tcacaacaat         180
gaaagatgct gcggacgccc tcaaagctgc tcacaaacac atggatgtcg atcaagttca         240
tgatatgatg gatgacattg ccgaacagca agatgtagct agagaaattt ctgatgccat         300
atccaaccca gttgcatttg gtcatgatat tgat                                    334

<210> SEQ ID NO 16
<211> LENGTH: 541
<212> TYPE: DNA
<213> ORGANISM: Monolepta hieroglyphica

<400> SEQUENCE: 16
atttgttgat actagtggta gacataaaca agaagaatca ctatttgaag aaatgttggc         60
agtttctaat gctgtgagac cagataatat tattttcgtt atggatgcaa ctattggtca        120
agcttgtgag tctcaggcta aagctttcaa agaaaaggta gatgtaggct ctgtaattat        180
aacaaaatta gatggacatg caaaaggagg tggtgcactc agtgctgtgg cagccactaa        240
cagtcctatt atattcattg gtacaggaga acatatagat gacttagaac ttttaaaac         300 aaaacctttc attagtaaat tattaggaat gggtgatata gaaggtttaa ttgataaagt        360
aaacgaatta agttagagg ataatgaaga attgttagaa aaaattaaac atgggcaatt        420
cacactcaga gacatgtatg aacagttcca aatatattatg aaaatgggac ctttctcaca       480
aataatggga atgatccctg gatttagcca agatttcatg tcaaaaggaa gtgaacaaga       540
a                                                                       541

<210> SEQ ID NO 17
```

```
<211> LENGTH: 394
<212> TYPE: DNA
<213> ORGANISM: Monolepta hieroglyphica

<400> SEQUENCE: 17
aataatggac agtatgaatg attatgaatt agataaccga gatggtgcaa aattatttac       60
aaagcaaaat ggtagagtta ttagagttgc acaagggtct ggtgttacag aaagagaagt      120
aaaagatttg atcacgcaat acacgaagtt tgccgccgta gtaaagaaaa tgggcggcat      180
aaagggtctt tttaaaggcg gcgatatggc taaaaatgtc aatcacaacc aaatggccaa      240
acttaatcaa caaatggcca agatgatgga tcctcgagtg cttcagcaaa tgggcggcat      300
ggctggatta cagaacatga tgagacagct acaagcgggc gcggcaggag gcttgggagg      360
tttgggtaac cttatgggtg gttttggagg gaaa                                  394
```